United States Patent [19]

Hansen et al.

[11] Patent Number: 4,613,938
[45] Date of Patent: Sep. 23, 1986

[54] PRESENT WEATHER OBSERVING SYSTEM UTILIZING PARTICULATE SIZE AND VELOCITY MEASUREMENTS

[75] Inventors: Donald F. Hansen, Needham; William K. Shubert, Acton, both of Mass.

[73] Assignee: HSS Inc., Bedford, Mass.

[21] Appl. No.: 695,169

[22] Filed: Jan. 25, 1985

[51] Int. Cl.[4] .................. G06F 15/54; G01W 1/00; G01N 21/51; G01N 15/02
[52] U.S. Cl. .................. 364/420; 73/170 R; 73/171; 250/574; 356/336; 356/338
[58] Field of Search ............. 364/420; 73/170 R, 171; 250/574; 356/336, 342, 338

[56] References Cited

U.S. PATENT DOCUMENTS

| | | | |
|---|---|---|---|
| 3,141,330 | 7/1964 | Murray et al. | 73/171 X |
| 4,010,357 | 3/1977 | Horner | 364/420 |
| 4,015,135 | 3/1977 | Tipton, Jr. | 250/574 |
| 4,099,875 | 7/1978 | McMahon et al. | 250/574 |
| 4,134,679 | 1/1979 | Wertheimer | 250/574 X |
| 4,154,089 | 5/1979 | Carlon | 73/29 |
| 4,329,054 | 5/1982 | Bachalo | 356/336 |
| 4,361,403 | 11/1982 | Loos | 250/574 X |
| 4,444,500 | 4/1984 | Flinsenberg et al. | 356/336 |
| 4,473,296 | 9/1984 | Shofner et al. | 356/336 |
| 4,497,577 | 2/1985 | Sato et al. | 250/574 X |
| 4,540,283 | 9/1985 | Bachalo | 356/336 |

OTHER PUBLICATIONS

Marshall, J. S. et al., "The Distribution of Raindrops with Size," *Journal of Meteorology*, vol. 5, Aug. 1948, 165-166.

Gunn, Ross et al., "The Terminal Velocity of Fall for Water Droplets in Stagnant Air," *Journal of Meteorology*, vol. 6, Aug. 1949, 243-8.

Gunn, K. L. S. et al., "The Distribution with Size of Aggregate Snowflakes," *Journal of Meteorology*, vol. 15, Oct. 1958, 452-461.

Drain, Leslie, E., "Doppler Velocimetry", *Laser Focus*, Oct. 1980, 68-79.

Federal Meteorological Handbook No. 1, Part B, Jul.-/Aug. 1976, B2-12, 13; B3-12, 16, 46, 47; B7-7, 8, 9.

*Primary Examiner*—Jerry Smith
*Assistant Examiner*—Clark A. Jablon
*Attorney, Agent, or Firm*—Joseph S. Iandiorio; William E. Noonan

[57] ABSTRACT

A present weather observing system including a radiation source for providing a beam of radiation in the atmosphere and a detector for detecting scattered radiation from suspended or precipitating particles within a sample volume, the detector having a field of view intersecting the beam to define the sample volume. The invention further includes a device for determining the size and velocity of at least one particle precipitating through the sample volume, and an element responsive to the device for determining size and velocity for identifying the type of precipitation.

38 Claims, 22 Drawing Figures

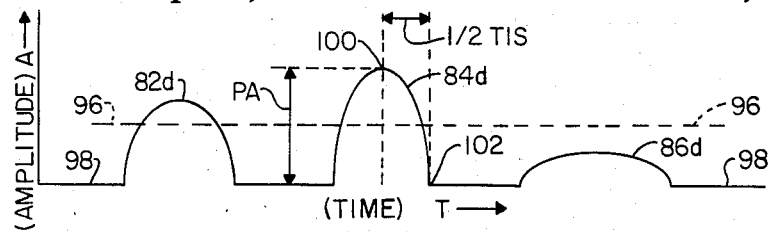
FIG. 4C
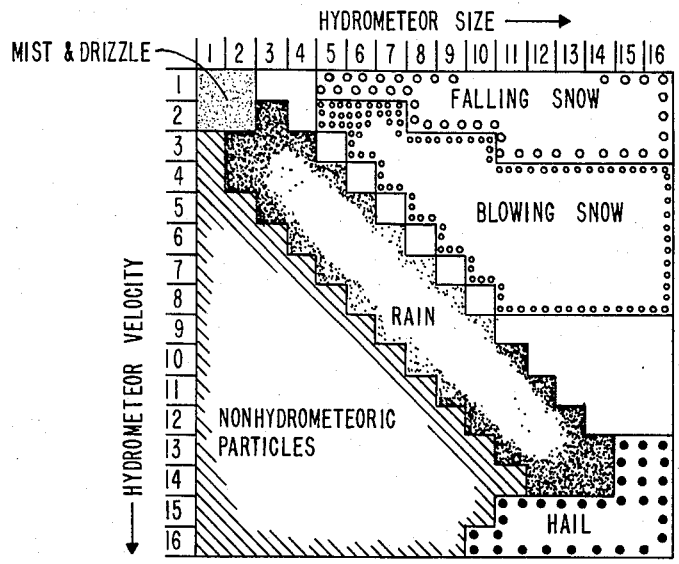
FIG. 5A
MATRIX SCALES
| COLUMNS NO. | EQUIVALENT PARTICLE RADIUS (MM) | ROWS NO. | PARTICLE VELOCITY (M/SEC) |
|---|---|---|---|
| 1 | < 0.10 | 1 | < .75 |
| 2 | .100 - .199 | 2 | .75 - 1.49 |
| 3 | .200 - .399 | 3 | 1.50 - 2.99 |
| 4 | .400 - .599 | 4 | 3.00 - 4.49 |
| 5 | .600 - .799 | 5 | 4.50 - 5.49 |
| 6 | .800 - .999 | 6 | 5.50 - 6.49 |
| 7 | 1.00 - 1.19 | 7 | 6.50 - 7.29 |
| 8 | 1.20 - 1.39 | 8 | 7.30 - 7.79 |
| 9 | 1.40 - 1.59 | 9 | 7.80 - 8.19 |
| 10 | 1.60 - 1.79 | 10 | 8.20 - 8.59 |
| 11 | 1.80 - 1.99 | 11 | 8.60 - 8.79 |
| 12 | 2.00 - 2.39 | 12 | 8.80 - 9.19 |
| 13 | 2.40 - 2.99 | 13 | 9.20 - 9.39 |
| 14 | 3.00 - 3.99 | 14 | 9.40 - 9.49 |
| 15 | 4.00 - 5.00 | 15 | 9.50 - 10.00 |
| 16 | > 5.00 | 16 | > 10.00 |
FIG. 5B

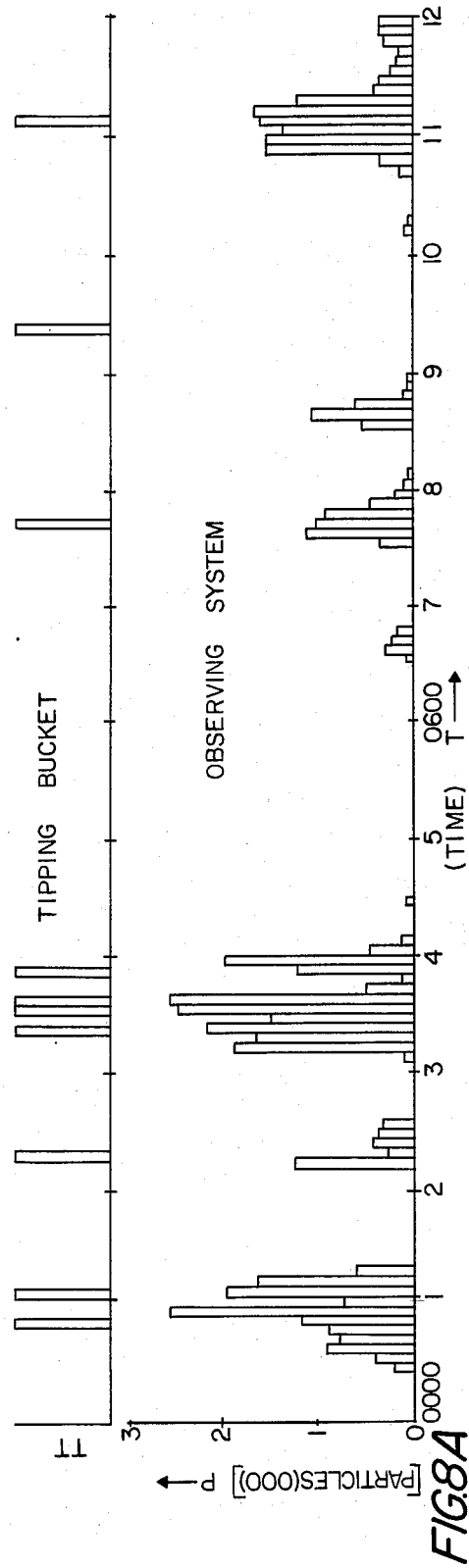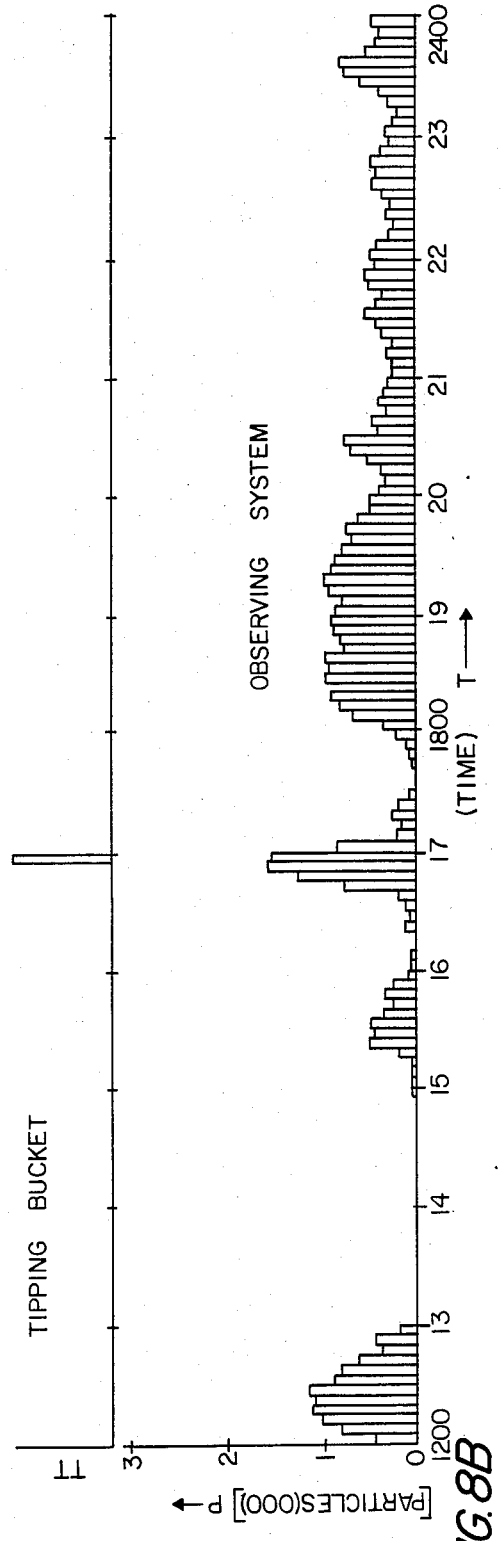
FIG.8A
FIG.8B

PRESENT WEATHER OBSERVING SYSTEM UTILIZING PARTICULATE SIZE AND VELOCITY MEASUREMENTS

FIELD OF INVENTION

This invention relates to a present weather observing system, and more particularly to an automated system for identifying the type of precipitation and ascertaining the amount and for defining visibility.

BACKGROUND OF INVENTION

Conventional instruments for monitoring atmospheric phenomena local to the instruments use a number of different approaches. The monitored phenomena include all forms of liquid and frozen precipitation, such as rain, drizzle, snow and hail, and also include those suspended particles classed as obstruction to vision, namely mist, fog, haze, dust and smoke. These phenomena are hereinafter referred to as present weather.

A number of devices measure the rate of precipitation, also known as the amount or intensity of precipitation. One instrument utilizes two oscillating reservoirs or "tipping buckets" to collect precipitation in a liquid state. A heater melts frozen precipitation into water. This instrument has a lengthy reporting interval during light precipitation and may under-represent the amount of blowing precipitation. Other devices use optical or electrical techniques to measure velocity of precipitation. Particles falling through an electrical field alter capacitance while particles descending through two or more light beams trigger each beam in sequence.

Visibility meters are routinely used to quantify the obstruction to vision, or in other words to measure the visual range during periods of reduced visibility. Several basic types of visibility meters are commercially available for that purpose such as transmissometers, forward scatter meters, backscatter meters, and integrating nephelometers. None of these types of instruments measures visibility directly. In all cases the instruments measure the atmospheric extinction coefficient, or are calibrated to provide the extinction coefficient from a measurement of the scattering coefficient. Visual range is then calculated using Koschmieder's Law (or a variant thereof) for daylight situations and Allard's Law (or a variant thereof) for nighttime situations.

Visibility meters as stand-alone sensors cannot identify the atmospheric phenomena which produce reduced visibility. For example, if the relative humidity were high and the temperature were well below zero the atmospheric phenomenon producing reduced visibility could be identified as snow; one could not, however, distinguish between the various forms of snow, or between snow and freezing fog or rain during those rare conditions where it rains well below the freezing point. As another example, if the temperature were well above freezing accompanied by a high relative humidity, the possible causes of reduction in visibility could be reduced to rain or fog but one would not be capable of distinguishing between those two phenomena.

These capabilities offer an extremely limited present weather capability fraught with ambiguous identifications. Furthermore, they offer no possible means for measuring the rate or quantity of precipitation.

Several systems for present weather observation are fully automated and provide rapid response to present weather occurrences. One such system, the Laser Weather Identifier (LWI) has an optical transmitter and receiver. The light transmitter is a chopped CW He-Ne laser. In one version the receiver consists of three independently mounted detecting telescopes. One telescope looks directly at the projected laser beam. The other telescopes are off-axis and are aimed at the midpoint of the laser beam to detect light scattered through small angles (0.6° and 1.2°). This design permits detection and identification of precipitation using scintillation, extinction and off-axis forward scatter effects on the laser beam. Precipitation is detected, identified and quantified strictly by the amount of scintillation produced in the signal of the on-axis detector. The sole function of the two off-axis detectors is to detect and identify fog. The LWI has false alarm problems when strong winds are present because the turbulent air induces scintillations in the laser beam which are mistaken for precipitation. The LWI also has difficulty measuring snow.

Another system is known as the Precipitation Occurrence Sensor System (POSS). The POSS utilizes a commercially available Doppler Radar pointed vertically. The vertically pointed radar measures the descent velocity of precipitation within a few meters of the ground to detect the occurrence of precipitation.

SUMMARY OF INVENTION

It is therefore an object of this invention to provide an improved present weather observing system for identifying a wide variety of types of precipitation.

It is a further object of this invention to provide such a system for determining size and velocity of precipitating particles.

It is a further object of this invention to provide such a system for resolving precipitating particles from suspended particles.

It is a further object of this invention to provide such a system for rapidly detecting the onset and cessation of precipitation.

It is a further object of this invention to provide an improved present weather observing system having minimal false readings due to wind, dew, frost, detector noise, or atmospheric radiation scintillations.

It is a further object of this invention to provide an improved present weather observing system for ascertaining the amount of precipitation.

It is a further object of this invention to provide such a system for discerning the volume of individual precipitating particles.

It is a further object of this invention to provide such an improved present weather observing system for determining the atmospheric extinction coefficient.

It is a further object of this invention to provide such a system for distinguishing the extinction coefficient due to precipitating particles from the total atmospheric extinction coefficient.

It is a further object of this invention to provide such a system that in combination with temperature and relative humidity sensors can identify the five basic obstructions to vision: mist, fog, haze, dust and smoke.

The invention includes means for providing a beam of radiation in the atmosphere, and means for detecting scattered radiation from suspended or precipitating particles within a sample volume and having a field of view intersecting the beam to define the sample volume. The invention further includes means for determining the size and velocity of at least one particle, or agglomeration of particles, precipitating through the sample volume, and means responsive to the means for determining size and velocity for identifying the type of precipitation.

In a preferred embodiment the means for determining size and velocity may include means for resolving a signal due to at least one precipitating particle from signals due to suspended particles. The resolving means may include means for setting a threshold above which a precipitating particle is resolved and means for maintaining the threshold above the level due to suspended particles. The means for determining size and velocity may include means for generating a peak signal value and means for generating a time-in-sample value. The identifying means includes means for matching size and velocity of the precipitating particle with predetermined values of precipitation particle sizes and velocities.

The resolving means may include means for distinguishing a precipitating particle signal greater than a predetermined magnitude from a predetermined particle signal less than the predetermined magnitude. The greater signal is due to a particle having a size larger than the predetermined magnitude; the lesser signal is due to a particle having a size smaller than the predetermined magnitude. The means for determining size and velocity may include means for generating a peak signal value having a first peak signal generator responsive to the greater signal and a second peak signal generator responsive to the lesser signal, and means for generating a time-in-sample value having a first time-in-sample generator responsive to the greater signal and a second time-in-sample generator responsive to the lesser signal.

The means for determining size and velocity may also include means for indicating the resolved precipitating particle signal and means for counting those indications. The identifying means may include means for matching size and velocity of the precipitating particle with first predetermined values for precipitation sizes and velocities for an indication rate less than a predetermined rate, and with second values for an indication rate greater than a predetermined rate. The observing system may further include means for ascertaining the amount of precipitation which may include means for discerning the volume of a precipitating particle and means for summing the volumes of more than one such particle over a known time period.

It is preferred that the means for providing a beam emit square-wave modulated radiation, particularly at the rate of 1-4 KHz. The means for determining size and velocity may include adjusting means for synchronizing the determining means with the pulse rate. The means for providing a beam may emit radiation having a wavelength selected from the visible and near-visible spectral regions and may include a light-emitting diode. The detecting means may have a field of view encompassing only forward scattering radiation, particularly radiation scattered forward at an average angle, or central scattering angle, of 30°-55° from the axis of the beam. The detecting means may include a photoelectric element, particularly a photovoltaic cell.

The detecting means may also include means for separating signals due to scattered radiation from signals due to ambient radiation. The means for separating signals may include an optical bandpass filter. The sample volume defined by the field of view and the beam of radiation may be in the range of 200-1000 ml. Resolving means may include rectifying means for inverting the negative peaks of signals from the detecting means, thereby doubling the effective sampling rate. The resolving means may also resolve the precipitating particle signal from signals due to signal noise created by the detecting means.

In another embodiment, the means for determining size and velocity includes means for resolving a signal due to at least one precipitating particle from signals due to suspended particles and due to signal noise created by the detecting means. There is also included means for defining the extinction coefficient which includes means, responsive to the detecting means, for subtracting signals due to scattered radiation detected when at least one precipitating particle is resolved, from scattered radiation detected during the remainder of the sampling period when such a particle is not resolved. The means for defining the extinction coefficient may include means responsive to the detecting means for providing the scattered radiation signals in DC analog form. The defining means may include means for averaging the scattered radiation signals and means for averaging the output of the subtracting means. The defining means may also include means for obtaining the total extinction coefficient from the average of the scattered radiation signals and means for obtaining the extinction coefficient due to suspended particles from the average of the output of the subtracting means. The present weather observing system may further include a humidity sensor for sensing relative humidity and means for identifying the type of suspended particles within the sample volume by matching the extinction coefficient due to suspended particles with predetermined values for types of suspended particles and with the relative humidity.

The invention also encompasses a method of identifying the type of precipitation including providing a beam of radiation in the atmosphere, detecting scattered radiation in a sample volume of the beam, and resolving at least one precipitating particle from suspended particles. There is also generated a peak signal value and a time-in-sample value for resolved particle signals. Particle size is determined from the peak signal value; velocity is determined from the time-in-sample value. The size and velocity of the particle are matched with predetermined values of precipitation particle sizes and velocities.

The method may further include discerning the volume of the precipitating particle and summing the volumes of more than one precipitating particle over a known time period to determine the amount of precipitation. The method may also include the steps of subtracting signals due to scattered radiation detected when at least one precipitating particle is resolved from scattered radiation detected during the remainder of a sampling period when such a particle is not resolved to provide signals due to suspended particles. The scattered radiation signals are averaged, as are the suspended-particle signals; the total extinction coefficient is obtained from the average of the scattered radiation signals and the extinction coefficient due to suspended particles is obtained from the average of the suspended-particle signals. The method may further include sensing the relative humidity and identifying the type of suspended particle within the sample volume by matching the extinction coefficient due to suspended particles with predetermined values for types of suspended particles and with the relative humidity.

DISCLOSURE OF PREFERRED EMBODIMENT

Other objects, features and advantages will occur from the following description of preferred embodiments and the accompanying drawings, in which:

FIG. 1 is a block diagram of the invention;

FIG. 2. is a schematic plan view of a beam source and detector;

FIG. 4C is an illustration of typical precipitating particle signals;

FIG. 5A is a matrix of predetermined values of precipitating particle sizes and velocities;

FIG. 5B depicts matrix scales as used in FIG. 5A;

Figure 6:
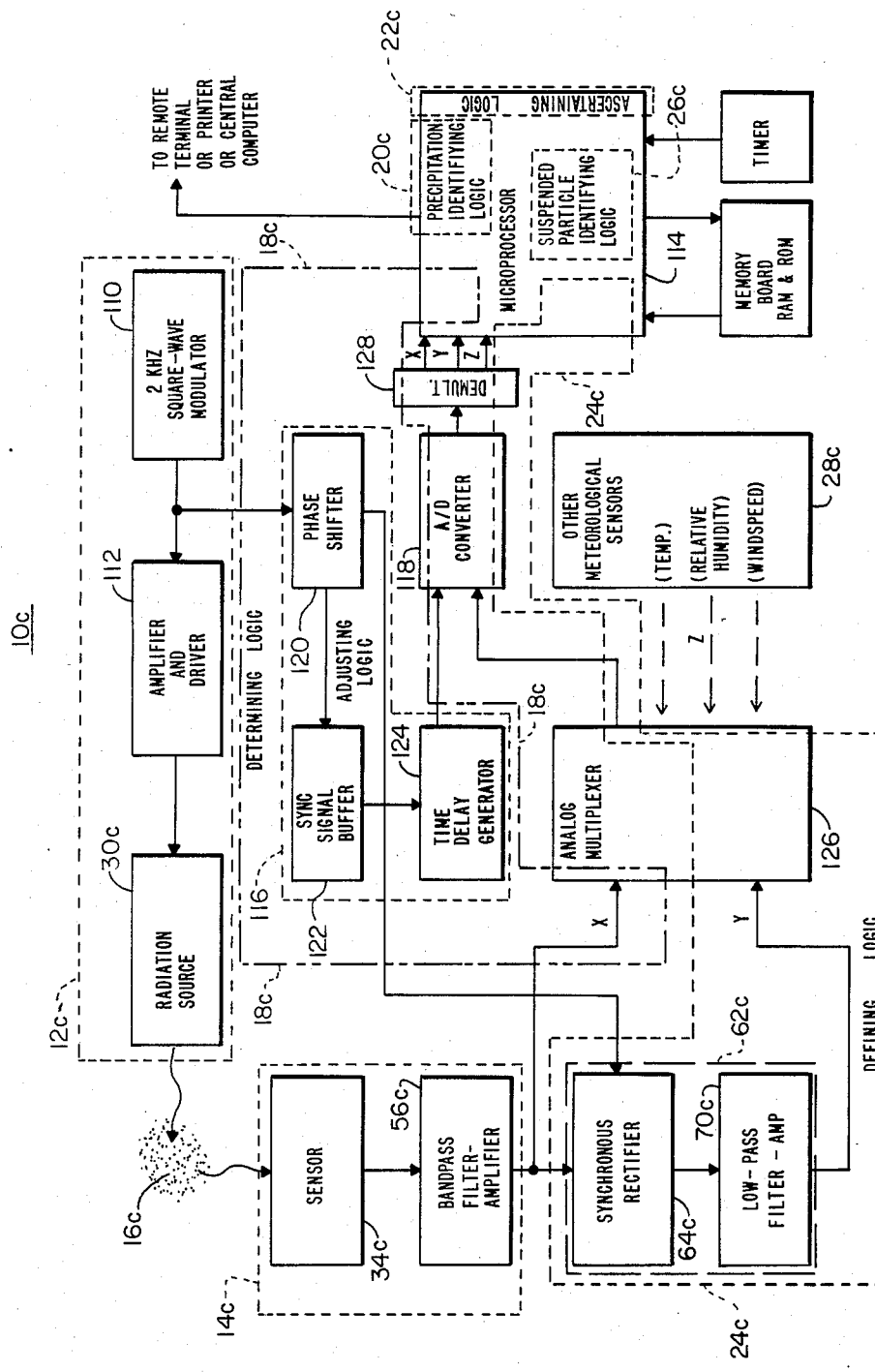
FIG. 6 is a block diagram of one embodiment of the invention.
Figure 7A:
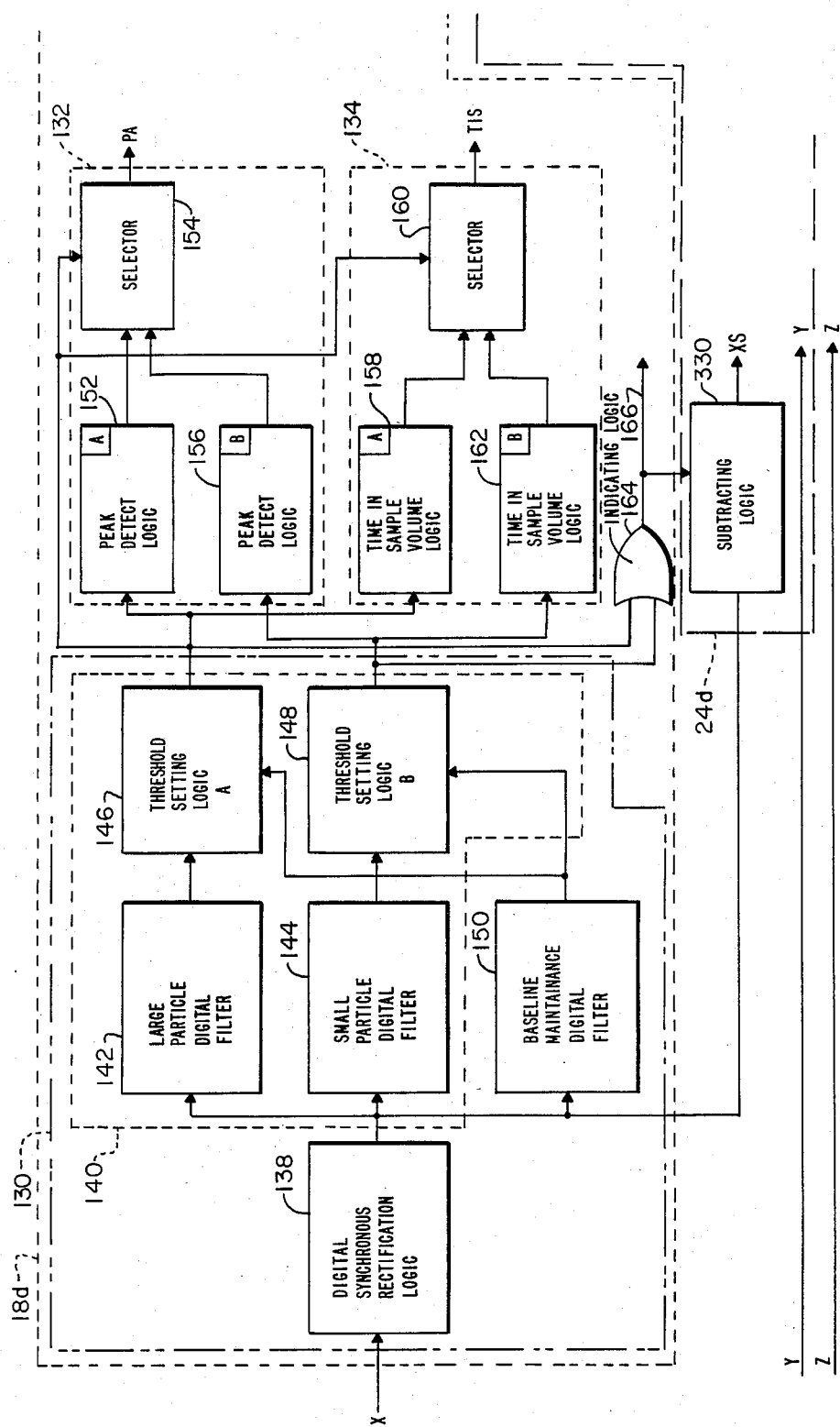
Figure 9:
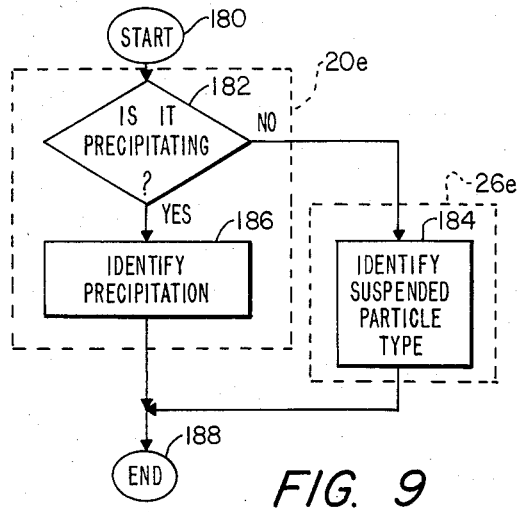
Figure 10:
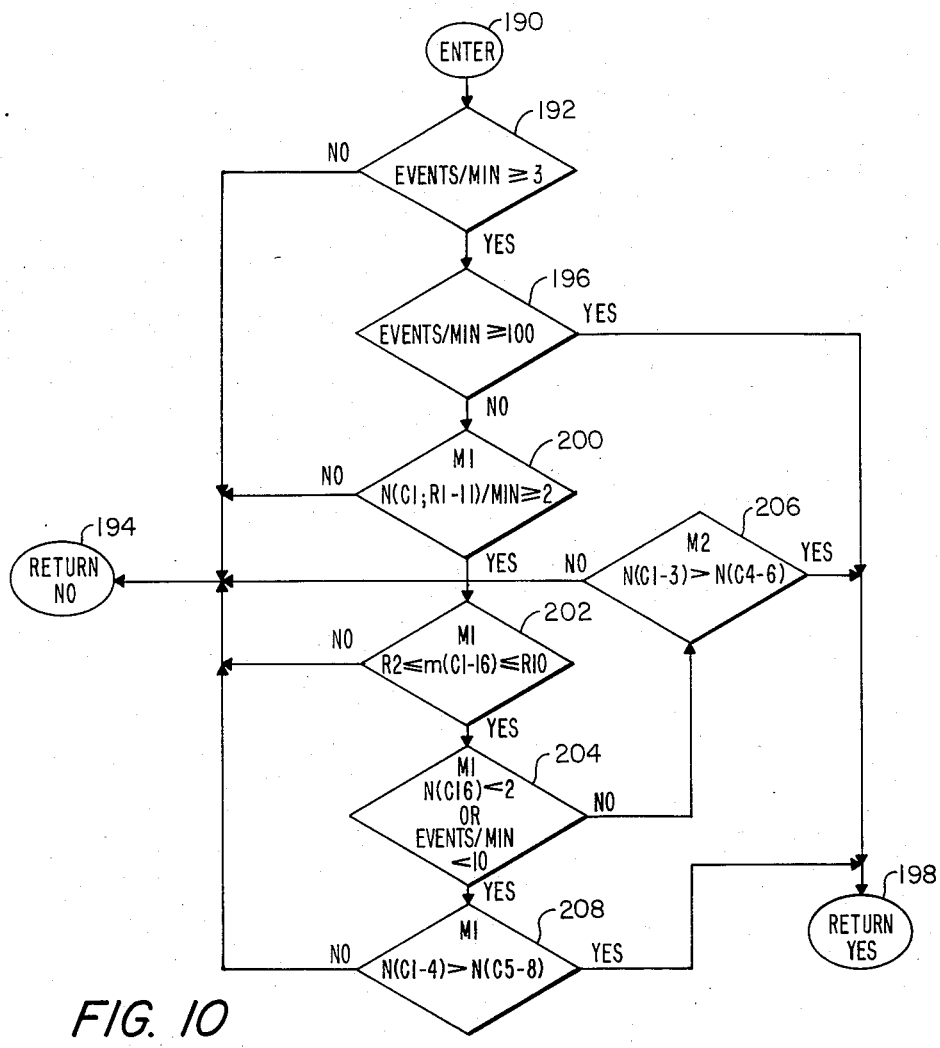
Figure 11:
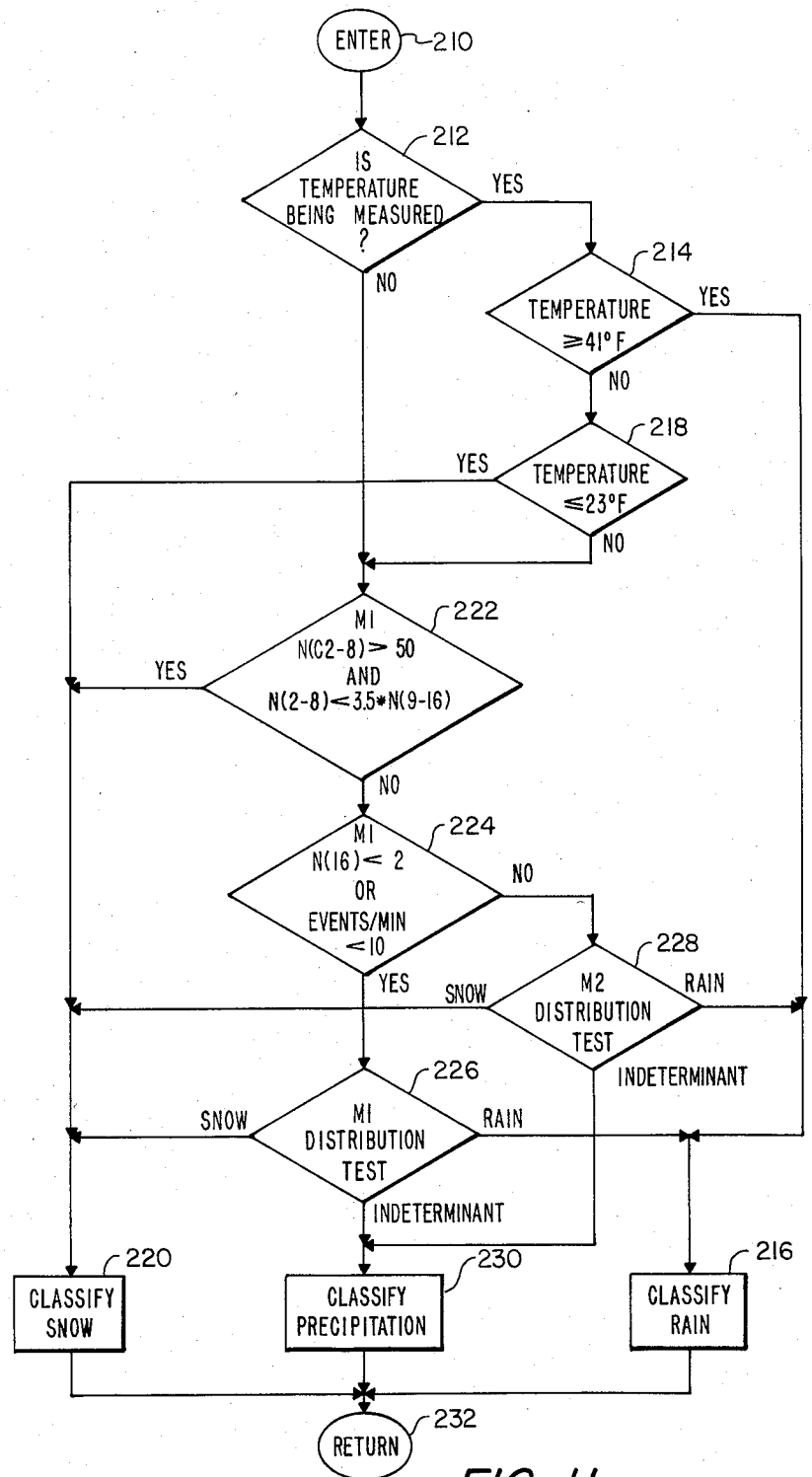
Figure 12A:
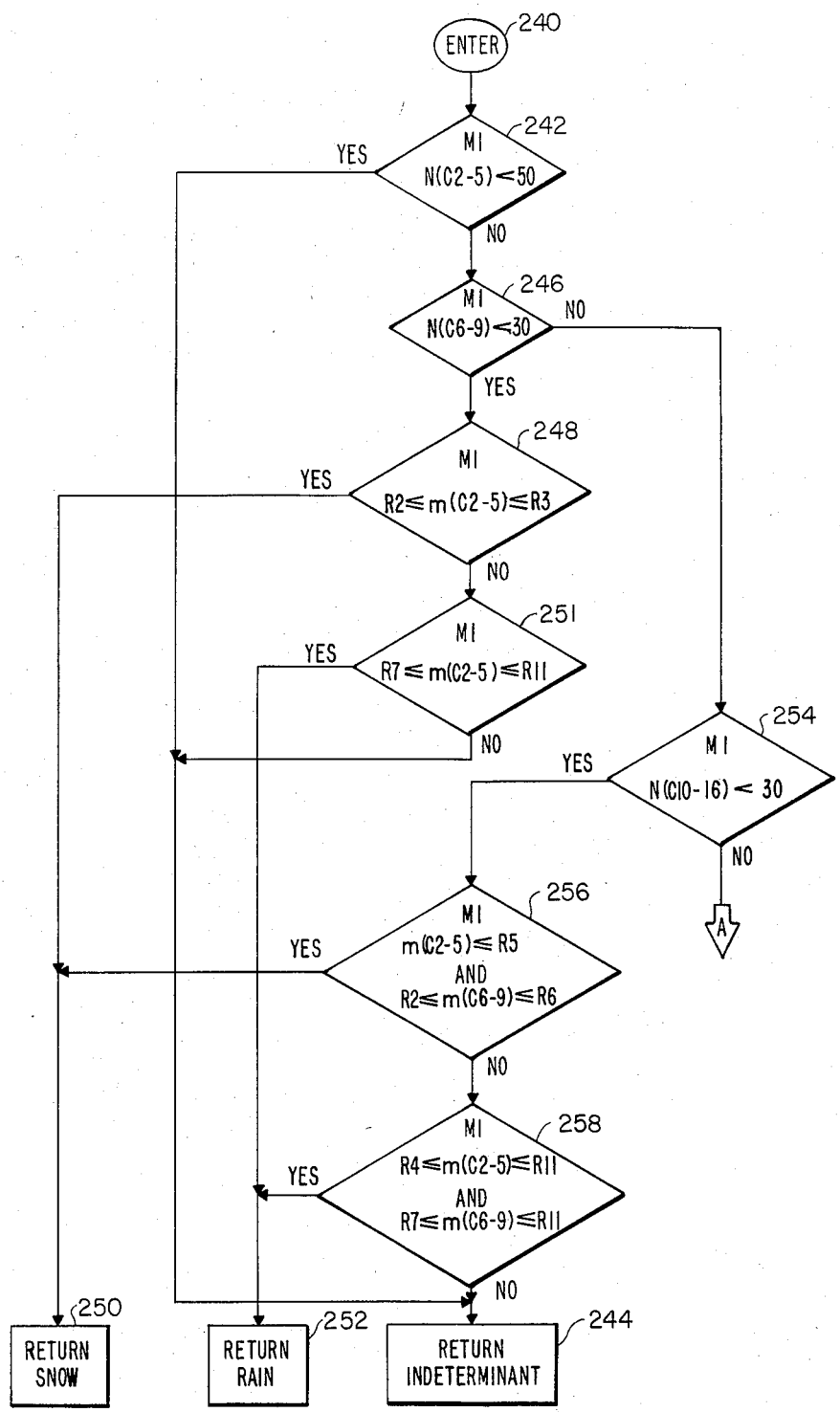
Figure 12B:
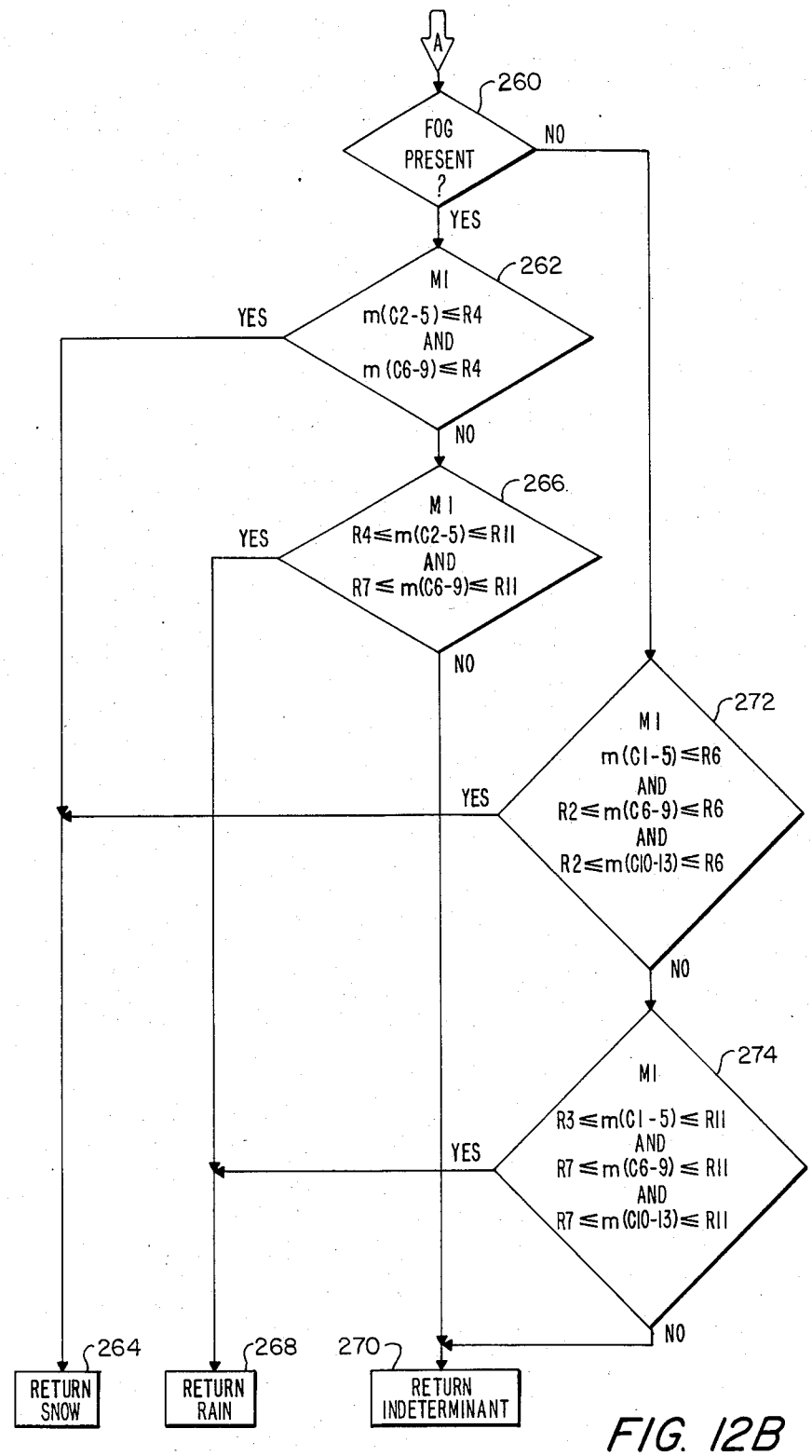
Figure 13A:
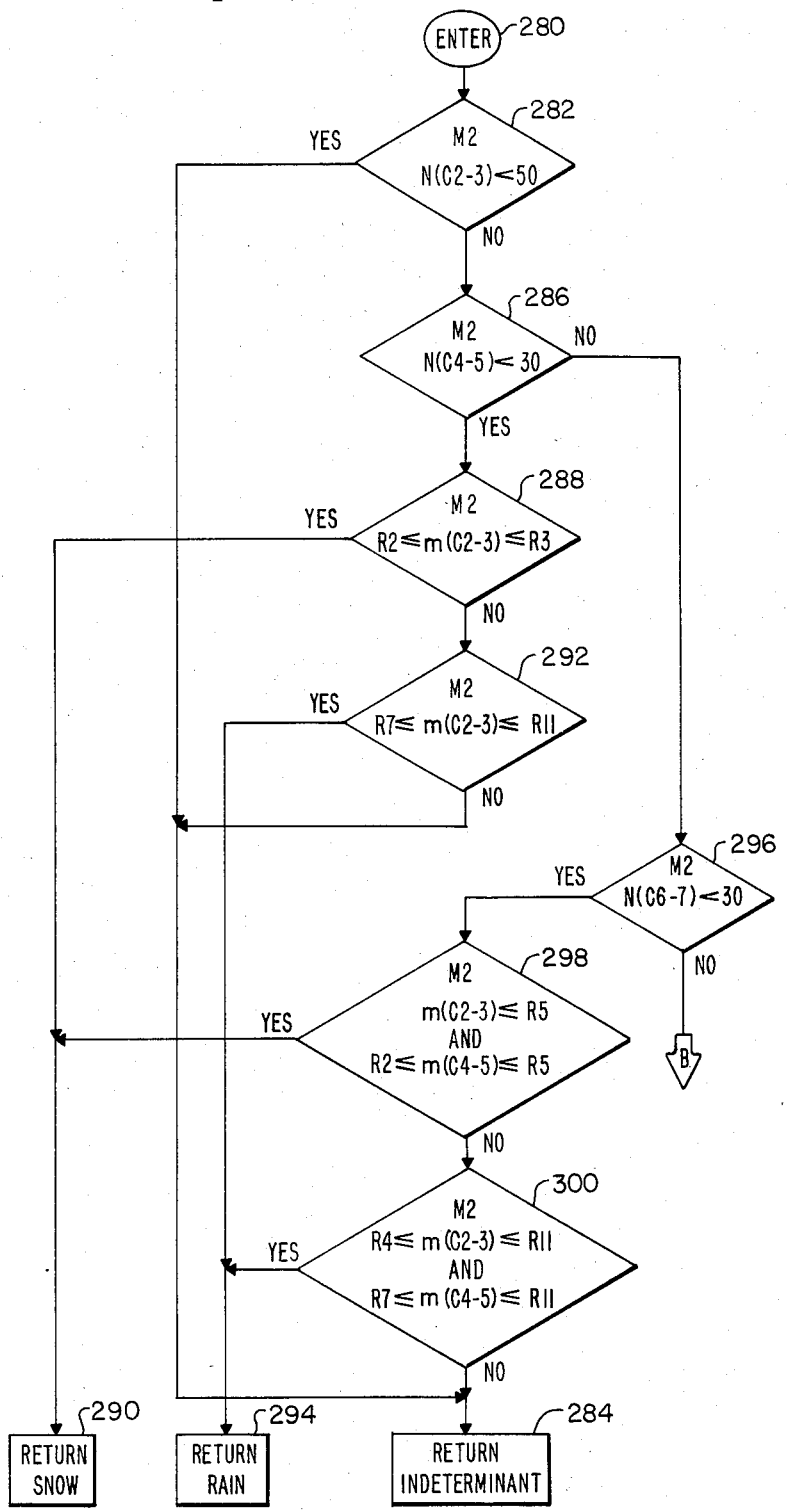
Figure 13B:
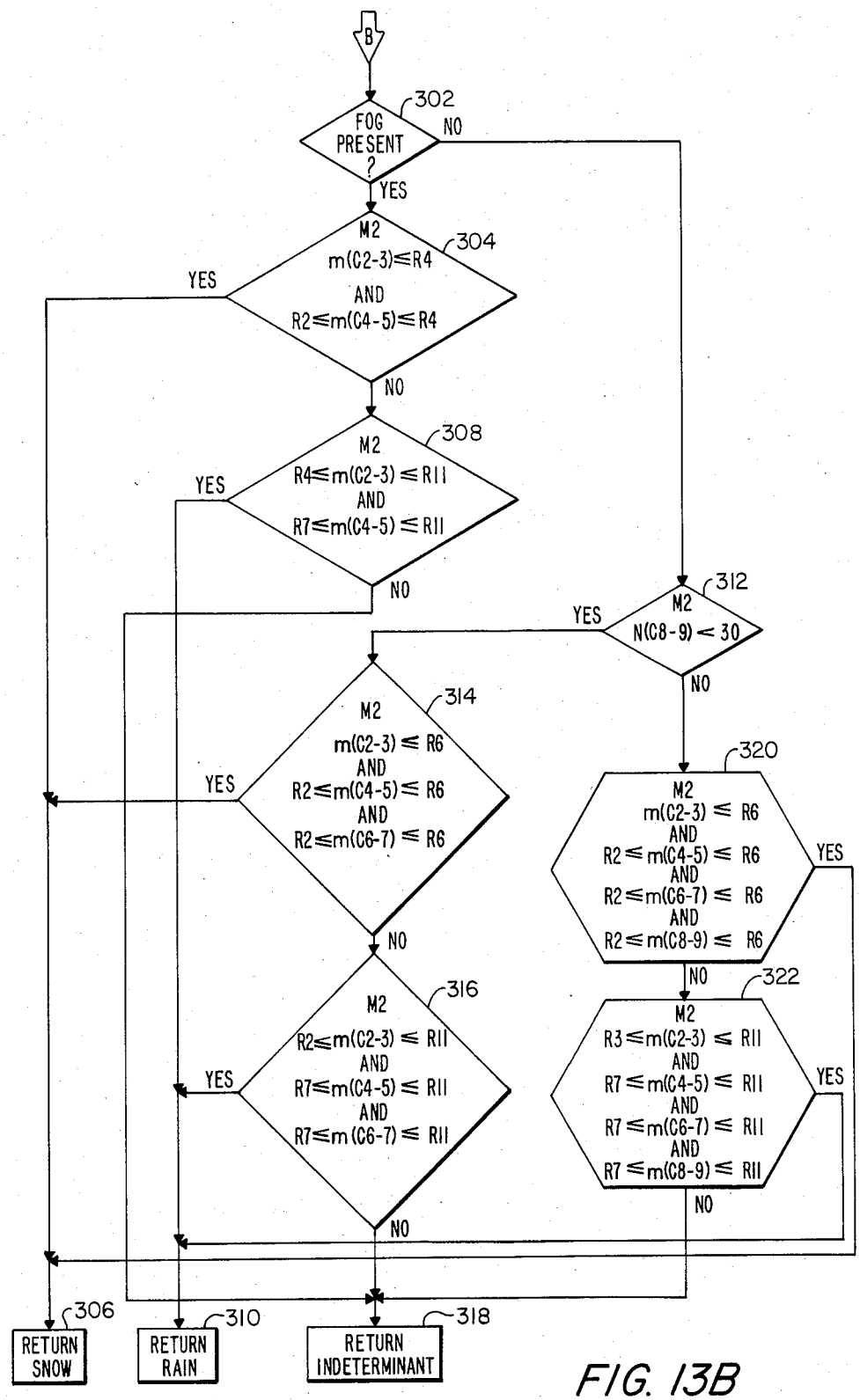
Figure 14A:
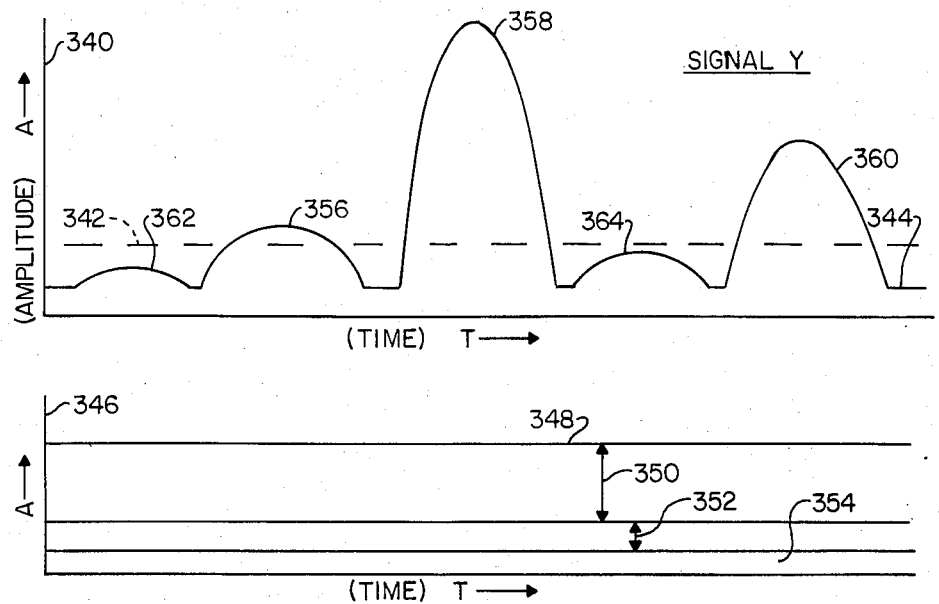

FIGS. 7A and B are more detailed views of a portion of FIG. 6;

FIGS. 8A and 8B show the response of a conventional tipping bucket rain gauge and the response of the invention over a twenty-four hour period;

FIG. 9 is a simplified flow chart for determination of present weather according to the invention;

FIG. 10 is a flow chart of a precipitation determination subroutine;

FIG. 11 is a flow chart of a precipitation identification subroutine;

FIGS. 12A and 12B are flow charts of a precipitation identification subroutine using a first set of values;

FIGS. 13A and 13B are flow charts of a precipitation identification subroutine using a second set of values;

FIG. 14A is an illustration of averaging scattered radiation signals; and

Figure 14B:
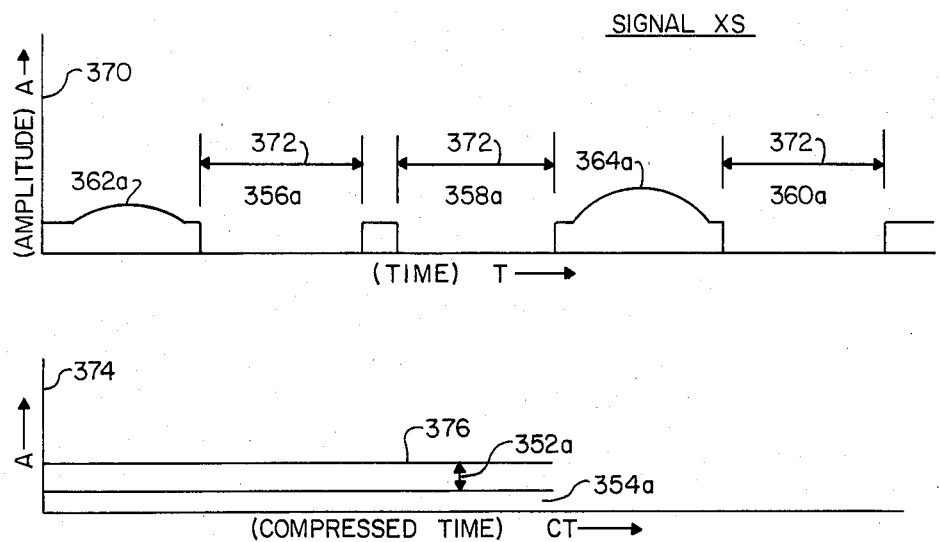

FIG. 14B is an illustration of averaging the output of the subtracting means.

Figure 1:
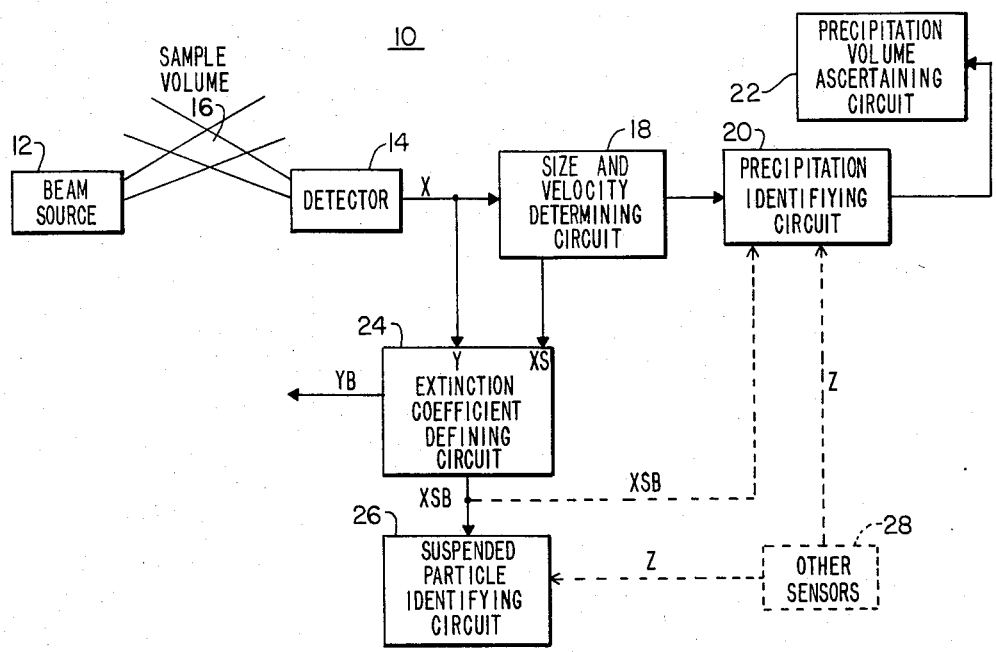

Present weather observing system 10, FIG. 1, includes an optical sensing subsystem having beam source 12, which emits a narrow beam intersected by the field of view of detector 14 to define sample volume 16. Detector 14 detects radiation scattered by suspended or precipitating particles within sample volume 16 and submits signal X to a signal processing subsystem including determining circuit 18, a means for determining size and velocity. Precipitation identification circuit 20, which identifies the type of precipitation within sample volume 16, is responsive to determining circuit 18.

Observing system 10 may include precipitation volume determining circuit 22, which ascertains the amount of precipitation and which is responsive to identification circuit 20. Observing system 10 may also include extinction coefficient defining circuit 24, which determines the extinction coefficient. Defining circuit 24 produces signal Y, used by that circuit to define the total atmospheric extinction coefficient, signal YB. In combination with determining circuit 18, defining circuit 24 produces signal XS, used to define the extinction coefficient due to suspended particles, signal XSB.

Observing system 10 may further include suspended particle identifying circuit 26, which identifies the type of suspended particles, such as haze, smoke, dust, fog or mist, causing obstruction to vision. Other meteorological sensors 28, shown in phantom, may provide signal Z to suspended particle identifying circuit 26 and to precipitation identification circuit 20. Signal XSB representing the extinction coefficient due to suspended particles may also be sent to precipitation identification circuit 20. The creation and processing of these signals is described below.

Figure 2:
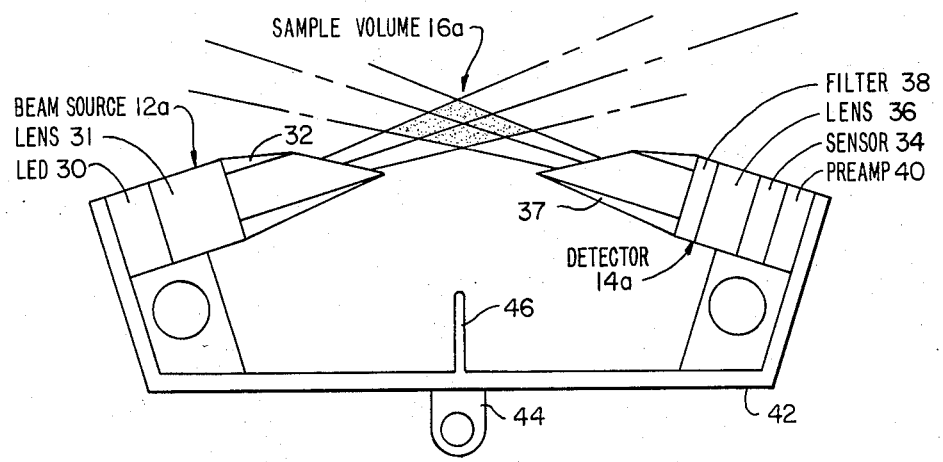

There is shown in FIG. 2 one embodiment of the optical sensing subsystem used in the present invention. Beam source 12a emits radiation having a wavelength selected from invisible and near-visible spectra and includes radiation source 30 having a light-emitting diode or infrared-emitting diode, such as a near-infrared diode emitting radiation having a wavelength of approximately 0.9 microns. Other wavelengths are acceptable for precipitation identification and volume ascertaining when the extinction coefficient need not be defined. The beam of radiation may be defined by lens 31, shade 32, or both. Detector 14a includes sensor 34 having a photoelectric element, particularly a silicon photovoltaic cell. Sample volume 16a is defined by a field of view created by lens 36, shade 37, or both, permitting the detector to view a discrete region of the beam. Detector 14a includes filter 38, which passes radiation having the wavelength of radiation source 30, and pre-amplifier 40. When a precipitating particle such as a raindrop passes through sample volume 16a, a signal pulse is generated by sensor 34.

The amplitude of the signal pulse is proportional to the square of the radius of the raindrop and the duration of the pulse is inversely related to the velocity of the drop. Since the observing system is capable of operating outdoors twenty-four hours a day, it must be capable of measuring signal pulse characteristics in the presence of ambient daylight. A non-modulated, or DC, radiation source 30 could be employed as the radiation source to provide signal X having a particular amplitude and duration for each event within the sample volume. However, the use of a modulated, or AC, radiation source, preferably square-wave modulated with a 50% duty cycle, and synchronous detection greatly enhances the signal-to-noise ratio in the receiver electronics, thus permitting measurements of suspended particles to be made with a greater degree of accuracy than permitted by a DC source. The signal-to-noise ratio is less important for signals representing precipitating particles because of their larger pulse amplitudes.

When a modulated radiation source is employed, the modulation frequency must be high enough to allow accurate measurement of the amplitude and duration of a signal pulse created by a precipitating particle. The peak of each oscillation defines a pulse envelope. The number of oscillations superimposed on the signal pulse envelope by the modulation frequency must be large enough that the oscillations do not distort the shape of the pulse envelope by an undue amount.

Radiation source 30 may be modulated at 1–4 kHz, preferably at 2–3 kHz, depending on the processing speed of the determining, identifying, and defining circuits. Higher processing speeds allow higher modulation frequencies. This modulation rate is also advantageous because it avoids false readings caused by sunlight flickering off objects external to the observing system.

Both beam source 12a and detector 14a are mounted on support bracket 42 having mounting means 44 and a calibrator mount 46 for checking instrument calibration. This arrangement may be adapted from the VR- 301 visibility meter manufactured by HSS, Inc. Sample volume 16a is selected in view of two opposing requirements. The larger the sample volume, the shorter the time period in which a representative sampling of particle sizes and velocities may be obtained. On the other hand, the sample volume must be small enough to assure a high probability that only one particle is passing through at a time; otherwise the size and velocity of each individual particle cannot be established. These requirements are satisfied for sample volumes of 200-1000 ml, particularly in the vicinity of one-half liter. Sample volumes of lesser size can be employed if sampling is made for a longer period of time. When the sample volume is larger, one or more small droplets may be present in a sample volume during the same time as a large droplet. The signal from a large precipitating particle, however, dominates to such an extent that there will be essentially no loss in measured accuracy of precipitation identification or quantification, by the fact that the signals from the two particles overlap.

Detector 14a is located several feet from beam source 12a and is situated to receive scattered radiation. To avoid the diffracted component of radiation created by raindrops, detecting means 14a is situated to receive radiation at scattering angles greater than 6°. The optimum forward scattering angles for determining visual range in the presence of suspended particles is 30°-55°. It is therefore preferred that detector 14a receive forward scattered radiation having a central or average scattering angle of 30°-55°. For precipitation identification and volume ascertaining, the useful range of scattering angles is much greater. Indeed, a field of view for receiving back-scatter radiation, having a central-scattering angle of 180°, suffices even for defining the extinction coefficient, though with less accuracy than a field of view for forward-scattered radiation.

Figure 3:
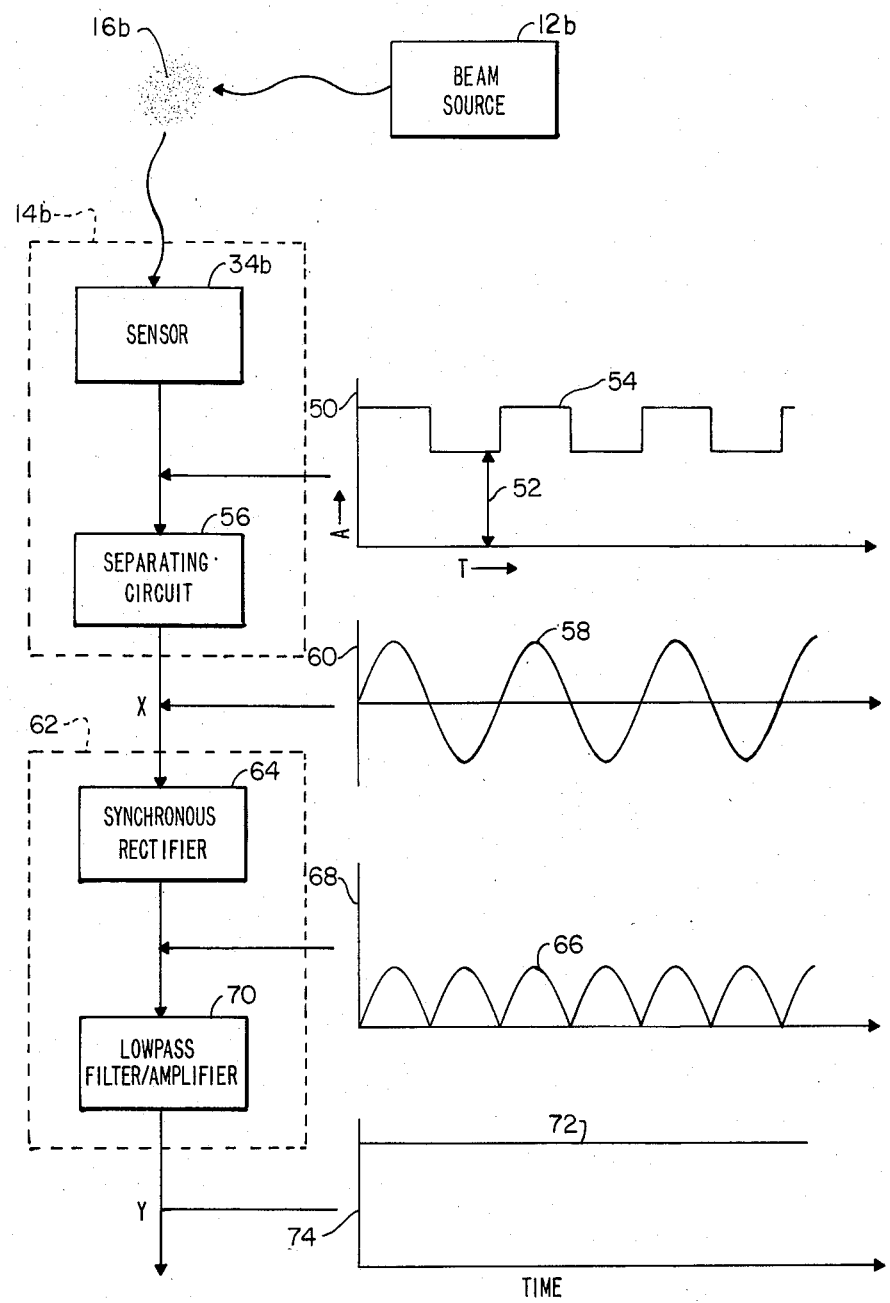
FIG. 3 is a block diagram of the electrical signal processing performed by one embodiment of the invention.

The signal processing as performed in one embodiment of the invention is shown in FIG. 3. A beam of radiation from beam source 12b strikes suspended particles within sample volume 16b. Scattered radiation is received by detector 14b. Beam source 12b includes a square wave-modulated radiation source in this embodiment and the signal produced by sensor 34b of detector 14b is illustrated in illustration 50 of FIG. 3. Illustrations 50, 60, 68 and 74 represent amplitude A, or signal intensity, over time T. Ambient light produces a non-modulated, DC signal 52. Scattered radiation from beam source 12b appears as square peaks 54 when sample volume 16b contains suspended particles only, that is, without precipitating particles passing through the sample volume. Detector 14b may include separating circuit 56, which separates signals due to scattered radiation from signals due to ambient radiation. Separating circuit 56 includes an electronic bandpass filter and amplifier which produces signal X shown as signal 58 in illustration 60. As shown in FIG. 1, detector 14 sends signal X to determining circuit 18 and may also send signal X to extinction coefficient defining circuit 24. Defining circuit 24 includes signal providing circuit 62, a means for providing a DC analog signal Y, as shown in FIG. 3. Signal providing circuit 62 includes synchronous rectifier 64 which inverts the negative peaks of signal X to create an additional set of positive peak values 66, as shown in illustration 68. Signal providing circuit 62 also includes a lowpass filter and amplifier 70, which produces a DC output signal Y, shown as curve 72 in illustration 74. Signal providing circuit 62 may be implemented in hardware or by a programmed microprocessor or other logic means.

Figure 4A:
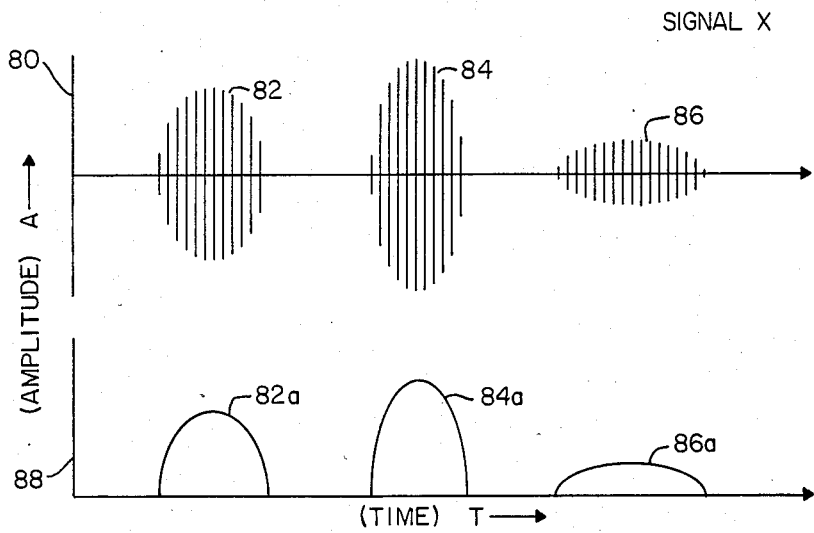
FIG. 4A is an illustration of signals resulting from precipitation particles without suspended particles present.
Figure 4B:
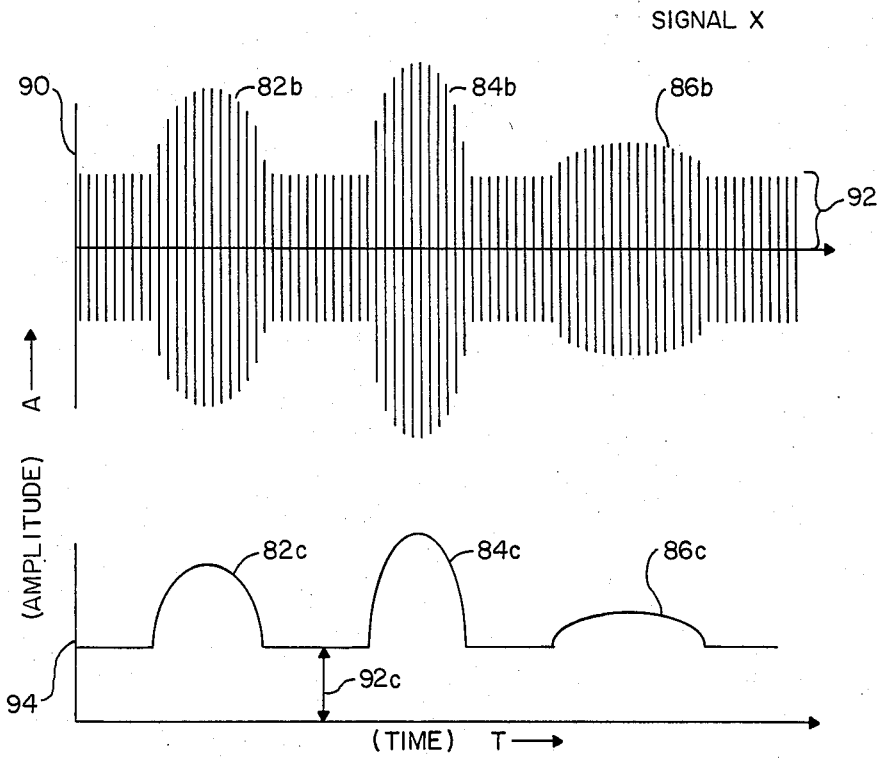
FIG. 4B is an illustration of signals due to both precipitating and suspended particles.

The variation in signal X resulting from precipitating particles passing through the sample volume without suspended particles present is shown in FIG. 4A, and the variation with suspended particles present is shown in FIG. 4B. FIGS. 4A and 4B show amplitude A versus time T for signal X from detector 14, FIG. 1. When modulated, signal X may be represented by pulses shown in illustration 80 as pulses 82, 84 and 86. Pulse 84 represents a large-sized drop, thus having a large amplitude. The relatively short duration of the pulse indicates a high velocity. Pulse 86 represents a very small drop or precipitating particle. The small size is indicated by the short peaks; the longer duration of the pulse indicates that this drop is also moving relatively slowly. Pulse 82 represents a particle of intermediate size and velocity. Illustration 88 represents the pulse envelopes sampled by size and velocity determining circuit 18, FIG. 1, indicated as pulse envelopes 82a, 84a and 86a. As shown in illustration 88, circuit 18 includes a synchronous rectifer which inverts the negative peaks.

Illustration 90, FIG. 4B, represents output signal X when suspended particles scatter radiation at a level indicated by amplitude 92. Pulses 82b, 84b and 86b rise in amplitude above amplitude 92. Illustration 94 represents the pulse envelopes for precipitating particle pulses 82c, 84c and 86c as they rise above suspended particle signals of amplitude 92c.

The processing of output signal Y for pulse envelopes 82d 84d and 86d is shown in FIG. 4C. As illustrated using pulse envelope 84d the size of the precipitating particle can be calculated from:

$$PA = KR^2$$

or $$R = \sqrt{PA/K}$$

where PA is the peak amplitude of the pulse, K is a calibration constant of proportionality, and R is the radius of the precipitating particle. Constant K is established by allowing a water drop of known size to fall through the sample volume and calibrating the invention accordingly. Peak amplitude PA may be generated using logic means which compares the latest signal value with a previous signal value when a modulated radiation source is used. If the new signal value is greater than the previous value the logic adopts the new value as the maximum signal value. The process is repeated until the peak value of the rectified AC signal is found.

The velocity of a precipitating particle may be determined from:

$$V = L/TIS$$

where V is the velocity of the particle, L is the path length in the sample volume, and TIS is the time-in-sample volume. A typical path length is 8 cm. To minimize false signals due to signal noise created by the detecting means, it is desirable to set threshold 96, above which a precipitating particle is resolved and below which a precipitating particle is not resolved. The time spent by a precipitating particle traversing the sample volume is measured by counting the number of data samples representing the rectified signal pulse. Time-in-sample volume TIS may be obtained by measuring the time for crossing threshold 96 until the amplitude returns to base line 98. A more accurate value of time-in-sample TIS is established by counting the number of samples from the time at which peak amplitude PA occurs at point 100 until the signal returns to base line 98 at point 102, then doubling that value to obtain the total TIS value. This technique is accurate in practice because the pulse envelope shape is nearly symmetrical about peak value 100.

As shown in FIG. 4C, pulse envelope 82d due to a medium-size particle and pulse envelope 84d due to a large-size particle are resolved, while pulse envelope 86d due to a very small-size particle is not resolved. Pulse envelope 86d is theoretically a very small particle, but having a very small amplitude it is possibly a noise fluctuation.

Threshold 96 is maintained above base line 98, which represents the signal due to suspended particles. When both threshold 96 and base line 98 are present, as shown in FIG. 4C, precipitating particles are resolved above threshold level 96, unresolved precipitating particles, which may possibly be signal noise, are located between threshold level 96 and base line 98, and signals due to suspended particles have an amplitude equal to base line 98.

There is shown in FIG. 5A an idealized set of predetermined values of precipitating particle sizes and velocities. The Marshall-Palmer raindrop size distribution described in J. S. Marshall and W. Mak Palmer, "The Distribution of Raindrops With Size", J. Meteor. 5: 165–166 (1948), is a convenient means for establishing the incremental dimensions of column size scales. The distribution shows that the size of raindrops varies with rain rate. Rain rate from 0.25 mm/hr to 100 mm/hr were used to determine the incremental size groups shown in FIG. 5B for particle sizes up to radii of 3 mm, as shown in columns 1–13. The physical limit to the diameter of raindrops is 5–6 mm. The increments for the velocity scale, shown in FIG. 5B as rows 1–16, was established using the Gunn-Kinzer measured velocities for raindrops in stagnant air, as described in R. Gunn and G. D. Kinzer, "The Terminal Velocity of Fall for Water Droplets in Stagnant Air", J. Meteor. 6: 243–248 (1949). Columns 14–16 on the size scale and rows 14–16 on the velocity scale were chosen to encompass the more common forms of hail. Since snow velocities are known to be low, on the order of 0.5–3.0 meters per second, they overlap with the velocities of very small raindrops. If raindrops behaved in the exact manner of the Marshall-Palmer and Gunn-Kinzer models, all raindrop measurements would fall in the data bins directly along the diagonal of FIG. 5A. In practice, several factors tend to disburse the size-velocity relationship from the idealized characterizations: the Marshall-Palmer size distribution for raindrops is only a best-fit approximation; winds and wind gusts can perturb the velocity-size relationship; and the shape of the sample volume can significantly influence the velocity-size characteristics of particles, since particles falling through a portion of the sample other than the center, or falling in other than a vertical direction because of wind, exhibit slightly different velocity-size characteristics, depending upon the shape of the sample volume and the direction of the wind. The diagonal portion of FIG. 5A depicts this spread of rain values among several bins, or sets of column and row values representing size and velocity values. Mist and drizzle having smaller sizes and velocities are located in the upper left-hand corner of FIG. 5A. Falling snowflakes have a low velocity yet a much larger apparent size than rain drops, as shown in the upper right-hand portion of FIG. 5A, while blowing snow has a similar size but a higher velocity. Hail tends to have both a larger size and a higher velocity than rain, as shown in the lower right-hand corner. Non-hydrometeoric particles, such as large dust particles or false alarms, are shown in the lower left-hand corner of FIG. 5A. As described below, other size and velocity increments may be utilized.

Present weather observing system 10c is shown in FIG. 6 in functional block diagram form. Beam source 12c emits pulsed radiation from radiation source 30c which strikes suspended or precipitating particles within sample volume 16c. Beam source 12c includes means for providing a modulated square wave 110. Radiation source 30c is responsive to amplifier and driver 112, which is in turn responsive to modulator 110. Scattered radiation is received by detector 14c, in which sensor 34c produces a signal from which signals due to ambient light are removed by electronic bandpass filter-amplifier 56c. The output of detector 14c, signal X, passes to size and velocity determining logic 18c. The embodiment of the present invention shown in FIG. 6 contains identifying logic 20c and further includes ascertaining logic 22c, defining logic 24c and suspended particle identifying logic 26c. Optional meteorological sensors 28c are also shown. Much of this embodiment is implemented in computer programs executed by microprocessor 114. Detector 14c also sends output X to DC analog signal providing logic 62c of extinction defining logic 24c. Phase shifter 120 of adjusting logic 116 coordinates modulator 110 with synchronous rectifier 64c of signal providing logic 62c and, through synchronous signal buffer 122 and time delay generator 124, with analog-to-digital converter 118. Analog multiplexer 126 receives signal X from detector 14c, signal Y from DC analog signal providing logic 62c and signal Z from optional meteorological sensors 28c. Signals X, Y and Z are submitted first to A-to-D converter 118, then to demultiplexer 128, which may be located within microprocessor 114. Demultiplexer 128 separates digitized signals X, Y and Z: signal X is used to resolve, measure the size of, and identify the type of precipitation; signal Y, derived from signal X, is used to determine the total extinction coefficient; and signal Z may be used in conjunction with other signals, as described below, for identification of suspended particles. Microprocessor 114 interacts with random access memory RAM, read only memory ROM, and a timer.

Figure 7B:
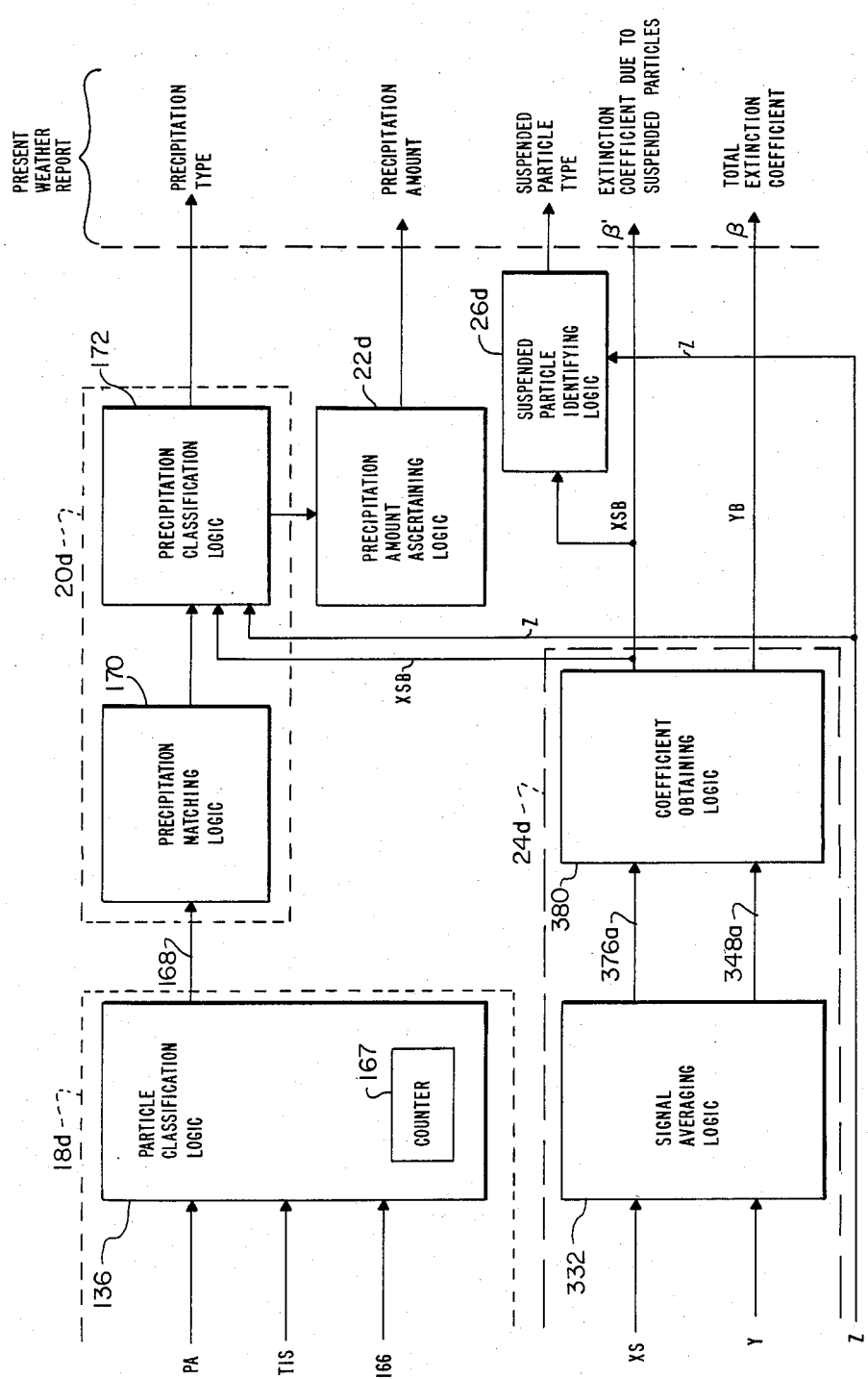

A functional block diagram of one embodiment of determining logic 18d, precipitation identifying logic 20d, precipitation amount ascertaining logic 22d, defining logic 24d, and suspended particle identifying logic 26d, is shown in FIGS. 7A and 7B. The elements and their functions as depicted in these figures are performed by logic means such as a microprocessor. Determining logic 18d includes resolver 130, logic 132 for generating a peak signal, logic 134 for generating a time-in-sample signal, and particle classification logic 136.

Signal X is shown entering digital synchronous rectification logic 138 and distinguishing logic 140 within resolver 130, FIG. 7A. Signal Z enters identifying logic 20d and suspended particle identifying logic 26d; signal Y enters defining means 24d. Signals X, Y and Z are digitized in this embodiment. Digital synchronous rectification 138 inverts the negative peaks of signal X to create an additional set of positive peak values. Distinguishing logic 140 contains two sets of digital filters, large particle digital filter 142, and small particle digital filter 144. The function of these two particle filters is to provide the best possible signal-to-noise ratio for the particle size and velocity determining process. Noise is due either to ambient light incident on the detector during the daytime, or the inherent noise of the detector during the nighttime. The noise can be minimized by narrowing the band width of signal X, but narrowing creates a distortion of the pulse shape. Since the size of a precipitating particle is determined by the signal pulse amplitude and velocity is determined by the pulse duration, distortion of the pulse shape could lead to errors in the measurement of size and velocity. To overcome this problem, two sets of filters are used. Particles having small size and low velocity, such as drizzle particles, exhibit a small amplitude and long duration, thus permitting a narrow band width to be employed. In a preferred embodiment, the equivalent electronic band width of filter 144 is 0–40 Hz. Large and fast-moving particles, including most raindrops, or slow-moving particles with a large size, such as snowflakes, are processed by large particle filter 142. The equivalent electronic band width of filter 142 is 0–160 Hz. The greater band width of this filter introduces less distortion to the larger signal pulses, particularly to pulse amplitude, created by the large precipitating particles. The greater band width of this filter also passes more noise, and therefore threshold-setting logic 146 sets a higher threshold above which precipitating particles are resolved. Threshold setting logic 148 sets a lower threshold for filter 144, thus permitting resolver 130 to detect smaller particles. Large particles are handled by the A-path of logic while the small particles are processed by the B-path of logic. Precipitating particle signals greater than a predetermined magnitude are thus distinguished from signals less than the predetermined magnitude.

In a preferred embodiment, resolver 130 includes baseline maintenance filter 150. Baseline filter 150 accurately maintains a baseline above signals due to suspended particles. Its accuracy is accomplished by very narrow band width, approximately 0–5 Hz, which accommodates rapid variations in signals due to suspended particles, as evidenced by the variations in signal X. Whenever a precipitating particle is detected by either the A or B logic paths, the band width of baseline filter 150 is changed to a narrow band width of approximately 0.33 Hz, which reduces the effect of precipitating particles on the baseline. Threshold setting logic 146 and 148 then sets a threshold above the baseline provided by filter 150. The representation of a baseline produced by filter 150 is shown in FIG. 4C as baseline 98. Threshold setting logic 146 or 148, depending on the size and velocity of the precipitating particle, sets threshold 96, FIG. 4C.

Logic 132 for generating a peak signal value, FIG. 7A, compares the latest signal X value with the previous signal X value at a predetermined rate. As an example of this comparison rate, if the radiation source is modulated at 2 kHz, and rectification logic 138 rectifies that signal, signal values are compared each 1/4000 second. If a new signal value is greater than a previous signal value, logic 132 adopts the new value as the maximum signal value. The process is repeated until the peak value of rectified signal X is found. If a precipitating particle is detected by both A-path threshold logic 146 and B-path threshold logic 148, then the peak signal value as detected by peak detect logic 152 is adopted by selector 154. Peak values detected by peak detector logic 156 are adopted only if the B-path threshold is crossed and the A-path threshold is not crossed. Logic 134 for generating time-in-sample values functions in a similar manner. Signals crossing the A-path threshold are processed by time-in-sample logic 158 and selected by selector 160. When the B-path threshold is crossed, but not the A-path threshold, time-in-sample logic 162 determines the time-in-sample by the process illustrated in FIG. 4C and discussed above. Selector 154 emits peak amplitude signal PA, and selector 160 emits time-in-sample volume value TIS.

Each time a precipitating particle is resolved by resolver 130, indicating logic 164, as shown in FIG. 7A, emits signal 166 to particle classification logic 136, FIG. 7B. Upon receiving indicating signal 166, particle classification logic 136 processes signal TIS to obtain particle velocity and signal PA to determine size, as illustrated in FIG. 4C and described above. Logic 136 contains counter 167, a means for counting signal indications 166.

Classification logic 136 emits signal 168, representing a resolved particle having a discrete size and velocity, to identification logic 20d. In other words, signal 168 is a particle count identified by size and velocity. Within identification logic 20d, precipitation matching logic 170 matches the size and velocity of the precipitating particle with a set of predetermined values for precipitation sizes and velocities, such as those shown in FIGS. 5A and 5B. Logic 170 is thus a means for matching size and velocity with predetermined values. The number of counts having a particular size and velocity is accumulated by matching logic 170.

Four separate examples of precipitation recognition matrices are shown in the matrices below, each five minutes in duration. A conventional 0.01 inch tipping bucket rain gauge was run simultaneously with the present invention. Table I shows a data matrix obtained for a light rain occurrence, where 268 drops were recorded:

TABLE I

| | \ DATA MATRIX FOR A LIGHT RAIN OCCURRENCE | | | | | | | | | | | | | | | | |
|---|---|---|---|---|---|---|---|---|---|---|---|---|---|---|---|---|---|
| | 250–350 | 350–422 | 422–460 | 460–503 | 503–548 | 548–598 | 598–652 | 652–711 | 711–775 | 775–846 | 846–922 | 922–1005 | 1005–1096 | 1096–1196 | 1196–1304 | 1304– | ROW SUM |
| 30–66 | 1 | 0 | 0 | 0 | 0 | 0 | 0 | 0 | 0 | 0 | 0 | 0 | 0 | 0 | 0 | 0 | 1 |
| 66–106 | 3 | 0 | 0 | 0 | 0 | 0 | 1 | 0 | 0 | 0 | 0 | 0 | 0 | 0 | 0 | 0 | 4 |
| 106–134 | 4 | 0 | 0 | 1 | 1 | 0 | 1 | 0 | 0 | 0 | 0 | 0 | 0 | 0 | 0 | 0 | 7 |
| 134–168 | 7 | 1 | 0 | 1 | 0 | 0 | 0 | 0 | 0 | 0 | 0 | 0 | 0 | 0 | 0 | 0 | 9 |
| 168–210 | 31 | 12 | 1 | 0 | 0 | 0 | 0 | 0 | 0 | 0 | 0 | 0 | 0 | 0 | 0 | 0 | 44 |
| 210–262 | 17 | 6 | 2 | 1 | 0 | 2 | 1 | 0 | 0 | 0 | 0 | 0 | 0 | 0 | 0 | 0 | 29 |
| 262–326 | *23 | *12 | 6 | 1 | 3 | 1 | 0 | 1 | 0 | 0 | 1 | 0 | 0 | 0 | 0 | 0 | 47 |
| 326–410 | 17 | 8 | *5 | *9 | 1 | 1 | *2 | *3 | 2 | 0 | 0 | 0 | 0 | 0 | 0 | 0 | 48 |
| 410–516 | 6 | 5 | 6 | 4 | *7 | *2 | 1 | 1 | *1 | 0 | 0 | 0 | 0 | 0 | 0 | 0 | 33 |
| 516–640 | 6 | 3 | 1 | 3 | 1 | 1 | 0 | 1 | 0 | 1 | 0 | 1 | 0 | 0 | 0 | 0 | 18 |

TABLE I-continued

| | \DATA MATRIX FOR A LIGHT RAIN OCCURRENCE | | | | | | | | | | | | | | | | |
|---|---|---|---|---|---|---|---|---|---|---|---|---|---|---|---|---|---|
| | 250–350 | 350–422 | 422–460 | 460–503 | 503–548 | 548–598 | 598–652 | 652–711 | 711–775 | 775–846 | 846–922 | 922–1005 | 1005–1096 | 1096–1196 | 1196–1304 | 1304– | ROW SUM |
| 640–800 | 5 | 1 | 0 | 0 | 0 | 0 | 0 | 0 | 0 | 0 | 0 | 0 | 0 | 0 | 0 | 0 | 6 |
| 800–1000 | 7 | 0 | 0 | 0 | 0 | 0 | 0 | 0 | 0 | 0 | 0 | 0 | 0 | 0 | 0 | 0 | 7 |
| 1000–1230 | 4 | 0 | 0 | 0 | 0 | 0 | 0 | 0 | 0 | 0 | 0 | 0 | 0 | 0 | 0 | 0 | 4 |
| 1230–1600 | 6 | 0 | 0 | 0 | 0 | 0 | 0 | 0 | 0 | 0 | 0 | 0 | 0 | 0 | 0 | 0 | 6 |
| 1600–2000 | 0 | 0 | 0 | 0 | 0 | 0 | 0 | 0 | 0 | 0 | 0 | 0 | 0 | 0 | 0 | 0 | 0 |
| 2000–9999 | 5 | 0 | 0 | 0 | 0 | 0 | 0 | 0 | 0 | 0 | 0 | 0 | 0 | 0 | 0 | 0 | 5 |
| COL-SUM | 141 | 48 | 21 | 20 | 13 | 7 | 6 | 6 | 3 | 1 | 1 | 1 | 0 | 0 | 0 | 0 | |

The column headings represent a radius interval of a precipitating particle in microns; the row headings represent velocity intervals in centimeters per second. The numbers within the matrix represent the number of counts of precipitating particles having that radius and velocity. The median particle velocities for the total number of particles in each column is indicated by an asterisk. The tipping bucket registered zero counts.

Table II depicts a data matrix of counts for a moderate rain occurrence, where a total of 1,811 drops were recorded:

A greater number of particles had a larger size than those in the light rain occurrence. The median size values also had slightly larger velocities than those for the light rain. The tipping bucket recorded one count.

There is shown in Table III a data matrix for a moderate snow occurrence, where 1754 snowflakes were recorded during a five-minute period:

TABLE III

| | DATA MATRIX FOR A MODERATE SNOW OCCURENCE | | | | | | | | | | | | | | | | |
|---|---|---|---|---|---|---|---|---|---|---|---|---|---|---|---|---|---|
| | 200–387 | 387–422 | 422–460 | 460–503 | 503–548 | 548–598 | 598–652 | 652–711 | 711–775 | 775–846 | 846–922 | 922–1005 | 1005–1096 | 1096–1196 | 1196–1304 | 1304– | ROW SUM |
| 30–66 | 78 | 27 | 23 | 25 | 30 | 29 | 30 | 35 | 21 | 28 | 15 | 19 | 12 | 16 | 8 | 28 | 424 |
| 66–106 | 90 | 33 | 29 | 29 | 17 | *36 | *23 | *13 | 13 | *19 | 15 | *18 | *10 | *5 | *14 | 22 | 386 |
| 106–134 | 68 | *20 | *13 | *16 | *16 | 15 | 8 | 14 | *10 | 10 | *9 | 6 | 5 | 7 | 4 | *16 | 237 |
| 134–168 | *52 | 12 | 8 | 7 | 14 | 8 | 6 | 6 | 7 | 7 | 8 | 5 | 5 | 6 | 15 | 173 | |
| 168–210 | 47 | 13 | 11 | 7 | 7 | 16 | 7 | 7 | 5 | 4 | 13 | 9 | 3 | 2 | 5 | 17 | 173 |
| 210–262 | 48 | 6 | 4 | 11 | 3 | 4 | 6 | 2 | 3 | 3 | 0 | 3 | 2 | 3 | 0 | 5 | 104 |
| 262–326 | 42 | 8 | 7 | 6 | 12 | 7 | 5 | 1 | 5 | 3 | 3 | 2 | 1 | 2 | 0 | 5 | 109 |
| 326–410 | 20 | 9 | 6 | 4 | 4 | 2 | 3 | 2 | 1 | 2 | 1 | 1 | 1 | 0 | 0 | 1 | 57 |
| 410–516 | 21 | 1 | 1 | 2 | 2 | 1 | 3 | 1 | 1 | 2 | 0 | 1 | 1 | 0 | 2 | 1 | 40 |
| 516–640 | 8 | 1 | 2 | 3 | 5 | 2 | 1 | 4 | 1 | 2 | 1 | 0 | 0 | 0 | 0 | 0 | 30 |
| 640–800 | 2 | 2 | 3 | 1 | 3 | 0 | 1 | 0 | 0 | 0 | 1 | 1 | 0 | 0 | 0 | 0 | 14 |
| 800–1000 | 1 | 1 | 2 | 2 | 1 | 0 | 0 | 0 | 0 | 0 | 0 | 0 | 0 | 0 | 0 | 0 | 7 |
| 1000–1230 | 0 | 0 | 0 | 0 | 0 | 0 | 0 | 0 | 0 | 0 | 0 | 0 | 0 | 0 | 0 | 0 | 0 |
| 1230–1600 | 0 | 0 | 0 | 0 | 0 | 0 | 0 | 0 | 0 | 0 | 0 | 0 | 0 | 0 | 0 | 0 | 0 |
| 1600–2000 | 0 | 0 | 0 | 0 | 0 | 0 | 0 | 0 | 0 | 0 | 0 | 0 | 0 | 0 | 0 | 0 | 0 |
| 2000–9999 | 0 | 0 | 0 | 0 | 0 | 0 | 0 | 0 | 0 | 0 | 0 | 0 | 0 | 0 | 0 | 0 | 0 |
| COL-SUM | 477 | 133 | 109 | 113 | 114 | 120 | 93 | 85 | 67 | 80 | 65 | 68 | 40 | 40 | 40 | 110 | |

Many counts were observed toward the right-hand side of the matrix, representing larger size radius values. Also, the median sizes had a far lower velocity than those of either the light or moderate rain. The tipping bucket registered two counts.

A false alarm occurrence is presented in Table IV:

TABLE II

| | DATA MATRIX OF COUNTS FOR A MODERATE RAIN OCCURENCE | | | | | | | | | | | | | | | | |
|---|---|---|---|---|---|---|---|---|---|---|---|---|---|---|---|---|---|
| | 250–350 | 350–422 | 422–460 | 460–503 | 503–548 | 548–598 | 598–652 | 652–711 | 711–775 | 775–846 | 846–922 | 922–1005 | 1005–1096 | 1096–1196 | 1196–1304 | 1304– | ROW SUM |
| 30–66 | 11 | 5 | 2 | 2 | 3 | 3 | 4 | 2 | 2 | 0 | 0 | 0 | 0 | 0 | 0 | 0 | 34 |
| 66–106 | 36 | 15 | 5 | 5 | 2 | 1 | 2 | 2 | 1 | 0 | 0 | 0 | 0 | 0 | 0 | 0 | 69 |
| 106–134 | 24 | 14 | 5 | 3 | 3 | 4 | 1 | 2 | 2 | 1 | 0 | 0 | 0 | 0 | 0 | 0 | 59 |
| 134–168 | 40 | 12 | 5 | 12 | 5 | 2 | 3 | 1 | 3 | 0 | 1 | 1 | 1 | 0 | 0 | 0 | 86 |
| 168–210 | 58 | 28 | 9 | 6 | 11 | 11 | 4 | 3 | 4 | 2 | 0 | 0 | 0 | 0 | 0 | 0 | 136 |
| 210–262 | 84 | 28 | 11 | 11 | 8 | 4 | 8 | 7 | 4 | 2 | 0 | 1 | 0 | 0 | 0 | 0 | 168 |
| 262–326 | *111 | *51 | 23 | 18 | 13 | 12 | 8 | 10 | 2 | 1 | 1 | 0 | 1 | 0 | 0 | 0 | 251 |
| 326–410 | 94 | 31 | 21 | *25 | 18 | 20 | 7 | 8 | 7 | 2 | 1 | 1 | 2 | 0 | 0 | 0 | 237 |
| 410–516 | 47 | 29 | *35 | 30 | *20 | *30 | *22 | *22 | *14 | *5 | 2 | 0 | *3 | 0 | 0 | 0 | 259 |
| 516–640 | 29 | 50 | 38 | 25 | 34 | 22 | 21 | 26 | 13 | 9 | *4 | *3 | 1 | 1 | 0 | 0 | 276 |
| 640–800 | 21 | 23 | 15 | 18 | 9 | 12 | 7 | 5 | 0 | 1 | 4 | 0 | 0 | 0 | 0 | 0 | 115 |
| 800–1000 | 26 | 9 | 6 | 2 | 4 | 2 | 1 | 1 | 0 | 0 | 0 | 0 | 0 | 0 | 0 | 0 | 51 |
| 1000–1230 | 12 | 0 | 2 | 3 | 1 | 0 | 0 | 0 | 0 | 0 | 0 | 0 | 0 | 0 | 0 | 0 | 18 |
| 1230–1600 | 35 | 1 | 1 | 0 | 0 | 0 | 0 | 0 | 0 | 0 | 0 | 0 | 0 | 0 | 0 | 0 | 37 |
| 1600–2000 | 0 | 0 | 0 | 0 | 0 | 0 | 0 | 0 | 0 | 0 | 0 | 0 | 0 | 0 | 0 | 0 | 0 |
| 2000–9999 | 15 | 0 | 0 | 0 | 0 | 0 | 0 | 0 | 0 | 0 | 0 | 0 | 0 | 0 | 0 | 0 | 15 |
| COL-SUM | 643 | 296 | 178 | 160 | 131 | 123 | 88 | 89 | 52 | 23 | 13 | 6 | 8 | 1 | 0 | 0 | |

TABLE IV

| | \multicolumn{17}{c}{DATA MATRIX FOR A FALSE ALARM OCCURENCE} | | | | | | | | | | | | | | | | |
|---|---|---|---|---|---|---|---|---|---|---|---|---|---|---|---|---|---|
| | 200-387 | 387-422 | 422-460 | 460-503 | 503-548 | 548-598 | 598-652 | 652-711 | 711-775 | 775-846 | 846-922 | 922-1005 | 1005-1096 | 1096-1196 | 1196-1304 | 1304 — | ROW SUM |
| 30-66 | 0 | 0 | 0 | 0 | 0 | 0 | 0 | 0 | 0 | 0 | 0 | 0 | 0 | 0 | 0 | 0 | 0 |
| 66-106 | 1 | 0 | 0 | 0 | 0 | 0 | 0 | 0 | 0 | 0 | 0 | 0 | 0 | 0 | 0 | 0 | 1 |
| 106-134 | 1 | 0 | 0 | 0 | 0 | 0 | 0 | 0 | 0 | 0 | 0 | 0 | 0 | 0 | 0 | 0 | 1 |
| 134-168 | 0 | 0 | 0 | 0 | 0 | 0 | 0 | 0 | 0 | 0 | 0 | 0 | 0 | 0 | 0 | 0 | 0 |
| 168-210 | 0 | 0 | 0 | 0 | 0 | 0 | 0 | 0 | 0 | 0 | 0 | 0 | 0 | 0 | 0 | 0 | 0 |
| 210-262 | 3 | 0 | 0 | 0 | 0 | 0 | 0 | 0 | 0 | 0 | 0 | 0 | 0 | 0 | 0 | 0 | 3 |
| 262-326 | 2 | 0 | 0 | 0 | 0 | 0 | 0 | 0 | 0 | 0 | 0 | 0 | 0 | 0 | 0 | 0 | 2 |
| 326-410 | 0 | 0 | 0 | 0 | 0 | 0 | 0 | 0 | 0 | 0 | 0 | 0 | 0 | 0 | 0 | 0 | 0 |
| 410-516 | 1 | 0 | 0 | 0 | 0 | 0 | 0 | 0 | 0 | 0 | 0 | 0 | 0 | 0 | 0 | 0 | 1 |
| 516-640 | 3 | 0 | 0 | 0 | 0 | 0 | 0 | 0 | 0 | 0 | 0 | 0 | 0 | 0 | 0 | 0 | 3 |
| 640-800 | 4 | 0 | 0 | 0 | 0 | 0 | 0 | 0 | 0 | 0 | 0 | 0 | 0 | 0 | 0 | 0 | 4 |
| 800-1000 | 7 | 0 | 0 | 0 | 0 | 0 | 0 | 0 | 0 | 0 | 0 | 0 | 0 | 0 | 0 | 0 | 7 |
| 1000-1230 | *6 | 0 | 0 | 0 | 0 | 0 | 0 | 0 | 0 | 0 | 0 | 0 | 0 | 0 | 0 | 0 | 6 |
| 1230-1600 | 11 | 0 | 0 | 0 | 0 | 0 | 0 | 0 | 0 | 0 | 0 | 0 | 0 | 0 | 0 | 0 | 11 |
| 1600-2000 | 0 | 0 | 0 | 0 | 0 | 0 | 0 | 0 | 0 | 0 | 0 | 0 | 0 | 0 | 0 | 0 | 0 |
| 2000-9999 | 12 | 0 | 0 | 0 | 0 | 0 | 0 | 0 | 0 | 0 | 0 | 0 | 0 | 0 | 0 | 0 | 12 |
| COL-SUM | 51 | 0 | 0 | 0 | 0 | 0 | 0 | 0 | 0 | 0 | 0 | 0 | 0 | 0 | 0 | 0 | |

Although 51 events were registered, all those events were located in the far left-hand column. Additionally, the median size in the far left-hand column had an unusually high velocity. Unusual event distributions such as these are detected as part of precipitation classification logic 172, as shown in FIG. 7B and described below. The response of an embodiment of the present weather observing system is presented with the response of a 0.01 inch tipping bucket rain gauge for a twenty-four hour period in FIGS. 8A and 8B. Time T in hours proceeds from zero hours to twelve hours in FIG. 8A, and then from twelve hours to twenty-four hours in FIG. 8B. The number of particles P is shown on the Y axis in thousands, that is, from zero to three thousand counts. TT represents the time of each tip of the tipping bucket rain gauge. As can be seen, the present invention provides a far more accurate indication of rain occurrence and, as will be described below, of precipitation amount.

Flow charts representing the function of precipitation identification logic 20e and suspended particle identification logic 26e are presented in FIGS. 9-13B. When initiated, step 180, logic 172 determines whether it is precipitating in step 182. If less than a minimum number of particles have been detected in step 182, then the suspended particle type is identified in step 184 as performed by suspended particle identifying logic 26e shown as logic 26d in FIG. 7B. If more than the minimum number of particles have been detected, such as at least fifteen particles in a five-minute sampling period, the next step is step 186, the identification of precipitation. At step 188, the function of identification logic 20e and discovery logic 26e is completed. Detailed steps within step 182 are described in FIG. 10; detailed steps within step 186 are depicted in FIG. 11. Step 184 is described below.

There is shown in FIG. 10 an expansion of step 182 of FIG. 9. After the commencement of step 182, step 190, the number of precipitating events per minute is examined in step 192. If there are less than three events per minute, a No is returned, step 194. If there are at least three events per minute, the logic proceeds to step 196. If there are at least one hundred events per minute, step 198 returns Yes because this high precipitation rate makes false events highly unlikely. False events may be caused by sunlight fickering off objects external to the system. If there are less than one hundred events per minute, at step 200 the number of counts within column 1, rows 1-11, of matrix M1 is examined.

Matrix M1 is an expanded version of matrix M2 (not shown). The rows matrices M1 and M2 are identical, but the column headings of matrix M1, representing particle radius, proceed from 250-350 microns in the first column to 1304 microns in the sixteenth column. The columns headings of matrix M2 proceed from 250-350 microns in the first column to 1303-1549 microns in the ninth column up to 4472 microns and beyond in the sixteenth column. As described below, matrix M1 is used for lighter rates of precipitation while matrix M2 is used for heavier precipitation.

If the number of events within column 1, rows 1-11 of matrix M1 are at least two per minute, in step 202 the position of the median values within matrix M1 is examined. If the median values in columns 1-16 are between row 2 and row 10, indicating a proper velocity of the particles, the next step is step 204. Otherwise, a No is returned in step 194. At step 204, the rate and size of precipitating particles are examined. If the number of events within column 16 are at least two, or there are at least ten events per minute, matrix M2 is utilized in step 206. In step 206, if the number of events in columns 1-3 are greater than the number of events within columns 4-6, step 198 returns a Yes, it is precipitating. If the requirements of step 206 are not satisfied, step 194 returns a No. If step 204 is satisfied, the number of events in matrix M1 within columns 1-4 is compared in step 208 to the number of events in columns 5-8. If these criteria are not satisfied, No is returned as step 194, and the next step is step 184 of FIG. 9, while if the criteria are satisfied, step 198 returns a Yes and proceeds to step 186 of FIG. 9.

If a Yes is returned in FIG. 10, step 198, the next step is step 186 of FIG. 9, which is shown in greater detail in FIG. 11. Commencement of step 198 of FIG. 10 begins step 210, FIG. 11. At step 212, it is determined whether signal Z is received by precipitation classification logic 172, FIG. 7B, and whether signal Z includes temperature measurements. If temperature is being measured, at step 214 an ambient temperature reading of at least 41° F. engages step 216, classifying the precipitation as rain. If the temperature is less than 41° F., where an ambient temperature reading less than or equal to 23° F. in step 218 activates step 220, where the precipitation is classified as snow. If at step 218 it is determined that the temperature is greater than 23° F., the next step is step 222. Within the scale of matrix M1, if the number of counts in columns 2-8 is greater than fifty and the number of counts in columns 2-8 is less than 3.5 multiplied by the number of counts within columns 9-16, then the precipitation is classified as snow, step 220. Otherwise, at step 224, if the number of counts within column 16 is less than two or the number of events per minute is less than ten, the following step is step 226, which is further described within FIGS. 12A and 12B. If neither of these two conditions is satisfied within step 224, step 228 is next, which is described in further detail in FIGS. 13A and 13B. If neither step 226 nor step 228 can accurately identify the type of precipitation, at step 230 the events are simply classified as precipitation. When the events have been classified as snow, rain, or precipitation, the subroutine ends, step 232.

When step 226, FIG. 11, is entered, the subroutine of FIGS. 12A and 12B begins at step 240, FIG. 12A. At step 242, if the number of counts within columns 2 through 5 of matrix M1 is less than fifty, an "indeterminate" classification is returned, step 244. If not, the number of counts within columns 6-9 is examined at step 246. If less than thirty events, the median values in columns 2-5 are examined in step 248. If the medians lie in row 2 or row 3, the precipitation is classified as snow, step 250. If not, and if the median values in columns 2-5 of matrix M1 lie between rows 7 and 11 inclusive, step 251 proceeds to step 252, where rain is classified. If not, step 251 proceeds to step 244, where an "indeterminate" reading is provided.

If at step 246 it is determined that there are at least thirty counts in columns 6-9 of matrix M1, the subroutine proceeds to step 254, where counts in columns 10-16 of matrix M1 of less than thirty engages step 256. If the median values in columns 2-5 lie within rows 1-5 and the median values in columns 6-9 lie between rows 2 and 6, inclusive, then snow is indicated, step 250. If not, at step 258 the median values in columns 2-5 lying between rows 4 and 11 inclusive, and the median values in columns 6-9 lying between rows 7 and 11 inclusive, indicate rain, step 252. Otherwise "indeterminate", step 244, is indicated.

If it is determined in step 254 that the number of counts within columns 10-16 are at least thirty, the subroutine proceeds to step 260 of FIG. 12B as indicated by arrow A. Step 260 determines whether fog is present by examining the value of signal XSB from defining means 24d shown in FIG. 7B. If the value of signal XSB, representing the extinction coefficient due to suspended particles, is equal to or greater than 1.5 plus the quantity 0.003 multiplied by the number of events per minute, fog is determined to be present for the purposes of this subroutine and a two-part test is made, step 262. If the median values of columns 2-5 in matrix M1 do not extend beyond row 4 and median values in columns 6-9 also do not extend beyond row 4, snow is indicated, step 264. Otherwise, at step 266, median values in columns 2-5 lying between rows 4-11 inclusive, and median values in columns 6-9 lying between rows 7-11 inclusive, indicate rain, step 268. If these conditions are not satisfied the subroutine indicates "indeterminate", step 270. If in step 260 fog is determined not to be present, three conditions must be satisfied in step 272. If the median values in columns 1-5 do not extend beyond row 6 and the median values in columns 6-9 lie between rows 2 and 6 inclusive, and median values in columns 10-13 lie between rows 2 and 6 inclusive, then snow is indicated, step 264. Otherwise at step 274 three more criteria are examined. If the median values in columns 1-5 lie between rows 3 and 11 inclusive and median values in columns 6-9 and columns 10-13 lie between rows 7 and 11 inclusive, rain is indicated in step 268. If not, the subroutine provides "indeterminate", step 270.

The steps within step 228 of FIG. 11, involving the matrix M2 distribution test, are depicted in FIG. 13A and 13B. Beginning at step 280, the subroutine proceeds to step 282, where the number of counts in columns 2-3 of less than fifty indicate "indeterminate", step 284. Otherwise, if the number of events within columns 4-5 is less than thirty, as determined in step 286, the median values in columns 2-3 are examined in step 288. If these median values lie within rows 2 and 3, snow is indicated, step 290. Otherwise, step 292 discerns whether the median values in columns 2-3 lie between rows 7 and 11 inclusive. If so, rain is indicated, step 294. Otherwise, "indeterminate" is returned, step 284. If in step 286 it is determined that there are at least thirty events within columns 4-5, the number of events in columns 6-7 is examined in step 296. If less than thirty, at step 298 the median values in columns 2-3 lying somewhere within rows 1-5 and median values in columns 4-5 lying between rows 2-5 inclusive, indicate snow, step 290. If these two conditions are not satisfied, in step 300 it is determined whether the median values in columns 2-3 lie between rows 4-11 and whether median values in columns 4-5 lie between rows 7 and 11 inclusive. Satisfaction of these conditions indicates rain at step 294; otherwise, "indeterminate" is returned, step 284.

If in step 296 it is determined that there are at least thirty events within columns 6-7, the subroutine proceeds to step 302 of FIG. 13B, as indicated by arrow B. The presence of fog is determined in a similar manner, as in step 260, FIG. 12B. If fog is present the median values in columns 2-3 lying at or less than row 4 and the median values in columns 4-5 lying between rows 2 and 4 inclusive indicates snow, step 306. If the two-part test of step 304 is not satisfied, at step 308 median values in columns 2 and 3 lying between rows 4 and 11 inclusive and median values in columns 4-5 lying between rows 7 and 11 inclusive indicates rain, step 310.

If it is determined in step 302 that fog is not present, the next step is step 312, where a number of events less than thirty within columns 8 and 9 require the three-part test of the matrix M2 distribution as determined in step 314. If the median values in columns 2-3 lie up to and including row 6, and the values in columns 4-5 and 6-7 lie between rows 2 and 6 inclusive, then snow is indicated, step 306. Otherwise, at step 316 in another three-part test, median values in columns 2-3 lying between rows 2-11 inclusive and median values in columns 4-5 and 6-7 lying between rows 7-11 inclusive indicate rain, step 310. Otherwise, "indeterminate" is indicated at step 318. If in step 312 it is determined that there are at least thirty events within columns 8 and 9, the subroutine proceeds to step 320 in which a four-part test ensues. If the median value within columns 2-3 lie within rows 1-6 and median values in columns 4-5, 6-7 and 8-9 lie within rows 2-6 inclusive, snow is indicated, step 306. Otherwise, in step 322 it is determined whether median values in columns 2-3 lie between rows 3 and 11 inclusive and median values in columns 4-5, 6-7 and 8-9 lie between rows 7-11 inclusive, which indicates rain, 310. If at least one of these steps is not satisfied, the subroutine proceeds to step 318, indicating indeterminate precipitation type.

The present weather observing system may further include precipitation amount ascertaining logic 22d, FIG. 7B, which ascertains the amount of precipitation accumulated during each set time period, typically every one to six minutes. Different ascertaining steps are used, depending upon the type of precipitation. For rainfall, the water content or volume of each resolved precipitating particle is ascertained and then summed with the volume of all the raindrops that have fallen through the sample volume. As described above for FIG. 4C, the amplitude of the signal generated by a raindrop is proportional to the square of the drop radius. The volume V of each drop is computed using the formula $$V = 4/3\pi r^3.$$

The total quantity of water W falling during a given time period is given by the expression:

$$W = \frac{K}{A} \sum_R \frac{4}{3} R^3 \cdot N(R)$$

where A is the cross-sectional area of the sample volume, that is, the area presented to the direction of rainfall, and N(R) is the number of raindrops of radius R that passed through the sample volume during the sampling time period. The constant K contains a calibration factor that is established either by comparison with an independent rain gauge or by dropping water drops of known size through the sample volume, and an additional factor to convert the physical dimensions of the drops and area into a standard reporting unit for rainfall, such as inches of water.

Frozen precipitating particles are sized by comparison with their raindrop equivalents. That is, a particle of frozen precipitation is taken to have the same size as a raindrop that produces the equivalent amplitude in signal X. After identifying the type of precipitation in precipitation identification logic 20d, FIG. 7B, the amount of fall of snow or other frozen precipitating particles is measured in terms of equivalent water content. Snowfall can be measured using an empirically established density factor applicable in general to all forms of snow, excluding ice pellets. The value of the density factor of snow in general is about 0.1. Thus if a given form of precipitation has been established as snow, the equivalent water content is found by first calculating the amount of water assuming spherical particles having a density of 1.0, then multiplying by the density factor to find the equivalent water content for the snow particle. If the basic form of precipitation is established, that is, whether the frozen precipitating particle is snow, snow pellets, snow grains or ice pellets, a more accurate method of determining equivalent water content may be used. An empirically established density factor may be obtained for each form of frozen precipitation and then multiplied by the calculated amount of water. A similar approach can also be applied to mixed forms of precipitation including liquid and frozen particles or combinations of frozen precipitation.

The present weather observing system may further include extinction coefficient defining logic 24d, as shown in FIGS. 7A and 7B. Defining logic 24d includes subtracting logic 330 as shown in FIG. 7A, which subtracts signals due to scattered radiation detected when at least one precipitating particle is resolved from scattered radiation detected during the remainder of the sampling period when such a particle is not resolved. Subtracting logic 330 eliminates the entire portion of signal X received from digital synchronous rectification 138 when indicating logic 164 indicates that a precipitating particle has been resolved. Subtracting logic 330 then emits signal XS, representing the extinction coefficient due to suspended particles only. In order to eliminate a signal during the time that a precipitating particle was in the sample volume, subtracting logic 330 goes backward in time a predetermined amount to remove the fraction of the particle signal that precedes the crossing of the detection threshold after the signal has crossed the base line.

Signals XS and Y are then sent to signal averaging logic 332 as shown in FIG. 7B. The logic steps within signal averaging logic 332 are illustrated in FIGS. 14A and 14B. The pulse envelopes representing signal Y are shown in illustration 340, which depicts amplitude A versus time T. Threshold 342 and base line 344 are shown. Illustration 346 shows signal 348 representing the average of signal Y over the time period of the sample, typically thirty seconds. Portion 350 of signal 348 is due to detected particles, while portion 352 is due to undetected particles. The signal due to suspended particles is indicated by portion 354. As shown in FIG. 14A, illustration 340, pulse envelopes 356, 358 and 360 represent detected or resolved particles, while pulse envelopes 362 and 364 represent undetected or unresolved particles. The portion of undetected particles in a given sample may be determined empirically.

The effect of subtracting logic 330 is shown in Illustration 370, FIG. 14B. Subtracting logic 330 removes time intervals 372, representing detected particles 356a, 358a and 360a. The remaining amplitude, due to undetected particles 362a and 364a, as well as the amplitude due to suspended particles, represents signal XS. Shown in illustration 374 is amplitude versus compressed time, where the running average does not include the time intervals 372. The average of signal XS is represented by signal 376, of which portion 352a is due to undetected particles and amplitude portion 354a is due to suspended particles.

Signal averaging logic 332, FIG. 7B emits signal 348a representing the average of signal Y, and signal 376a, representing the average of signal XS, to coefficient obtaining logic 380. Averaging logic 332 is thus a means for averaging scattered radiation signals Y and a means for averaging the output signal XS of subtracting logic 330. Coefficient obtaining logic 380 is a means for obtaining the total atmospheric extinction coefficient from the average of the scattered radiation signal 348a and a means for obtaining the extinction coefficient due to suspended particles as represented by average signal 376a. The extinction coefficient $\beta$ is obtained by multiplying signal S by a constant K, where S is signal 348a or signal 376a and K is a calibration constant chosen according to the visual range selected for observation. The visual range may be determined from a common variation of Koschmieder's law, where visual range VR equals $3/\beta$. For a visual range of 30 m to 300 km, a constant of approximately 10 is selected. A constant of 40 would provide an estimate of visual range from 7.5 m to 75 km. The present weather observing system is adjusted so that a known signal input differs from a reference standard by an amount equal to a multiplication constant K.

Suspended particle identifying logic 26d, FIG. 7B, relates the extinction coefficient due to suspended particles, signal XSB, to a given visibility condition prescribed by a conventional visibility code, such as the International Visibility Code. Suspended particles are identified by matching signal XSB with predetermined values for types of suspended particles and with the relative humidity through signal Z, as provided by a humidity sensor such as model HMP-lllA, available from Vaisala, Finland. For example, a high extinction coefficient value coupled with a high relative humidity normally indicates the presence of fog. Coupled with a low relative humidity, smoke or dust is indicated instead. Other meteorological sensors such as temperature sensors, signal Z, may be used in conjunction with the relative humidity and signal XSB.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A present weather observing system comprising:
    means for providing a beam of radiation in the atmosphere;
    means, having a field of view intersecting said beam to define a sample volume, for detecting scattered radiation from particles within said sample volume;
    means for determining the size and velocity of at least one particle precipitating through said sample volume; and
    means responsive to said means for determining size and velocity for identifying the type of precipitation.

2. The observing system of claim 1 in which the means for determining size and velocity includes means for resolving a signal due to at least one precipitating particle from signals due to suspended particles.

3. The observing system of claim 2 in which said resolving means includes means for setting a threshold above which a precipitating particle is resolved.

4. The observing system of claim 3 in which said resolving means includes means for maintaining said threshold above the level due to suspended particles.

5. The observing system of claim 2 in which said means for determining size and velocity includes means for generating a peak signal value and means for generating a time-in-sample value.

6. The observing system of claim 2 in which said identifying means includes means for matching size and velocity of said precipitating particle with predetermined values of precipitation particle sizes and velocities.

7. The observing system of claim 2 in which said resolving means includes means for distinguishing a precipitating particle signal greater than a predetermined magnitude from a precipitating particle signal less than the predetermined magnitude.

8. The observing system of claim 7 in which said greater signal is due to a particle having a size larger than said predetermined magnitude and said lesser signal is due to a particle having a size smaller than said predetermined magnitude.

9. The observing system of claim 7 in which said means for determining size and velocity includes:
    means for generating a peak signal value having a first peak signal generator responsive to said greater signal and a second peak signal generator responsive to said lesser signal; and
    means for generating a time-in-sample value having a first time-in-sample generator responsive to said greater signal and a second time-in-sample generator responsive to said lesser signal.

10. The observing system of claim 7 in which said means for determining size and velocity includes means for indicating said resolved precipitating particle signal and means for counting said indications.

11. The observing system of claim 10 in which said identifying means includes means for matching size and velocity of said precipitating particle with first predetermined values for precipitation sizes and velocities when an indication rate is less than a predetermined rate and with second values when the indication rate greater than a predetermined rate.

12. The observing sytem of claim 1 further including means, responsive to said means for identifying, for ascertaining the amount of precipitation.

13. The observing system of claim 12 in which said ascertaining means includes means for discerning the volume of said precipitating particle.

14. The observing system of claim 13 in which said ascertaining means includes means for summing the volumes of more than one precipitating particle over a known time period.

15. The observing system of claim 2 in which said means for providing a beam emits square-wave modulated radiation.

16. The observing system of claim 15 in which said radiation is emitted at a rate of one to four kilohertz.

17. The observing system of claim 15 in which said means for determining size and velocity includes adjusting means for synchronizing said determining means with said pulse rate.

18. The observing of claim 2 in which said means for providing a beam emits radiation having a wavelength selected from visible and near-visible spectral regions.

19. The observing system of claim 18 in which said means for providing a beam includes a light-emitting diode.

20. The observing system of claim 2 in which said detecting means has a field of view encompassing only the forward scattered radiation.

21. The observing system of claim 20 in which said field of view encompasses radiation scattered forward at an average angle of 30 to 55 degrees from the axis of said beam.

22. The observing system of claim 2 in which said detecting means includes a photoelectric element.

23. The observing system of claim 22 in which said photoelectric element is a photovoltaic cell.

24. The observing system of claim 2 in which said detecting means includes means for separating signals due to scattered radiation from signals due to ambient radiation.

25. The observing system of claim 24 in which said means for separating signals includes an optical bandpass filter.

26. The observing system of claim 2 in which said sample volume is in the range of two hundred to one thousand milliliters.

27. The observing system of claim 2 in which said resolving means includes rectifying means for inverting negative peaks of signals from said detecting means.

28. The observing system of claim 2 in which said resolving means also resolves the precipitating particle signal from signals due to signal noise created by said detecting means.

29. A present weather observing system comprising:
means for providing a modulated beam of radiation in the atmosphere;
means, having a field of view intersecting said beam to define a sample volume, for detecting scattered radiation from particles within said sample volume and having at least one photoelectric element;
means, responsive to said detecting means, for determining size and velocity of at least one particle precipitating through said sample volume, said means for determining size and velocity including means for resolving a signal due to at least one precipitating particle from signals due to suspended particles and due to signal noise created by said detecting means; and
means, responsive to said detecting means and said means for determining size and velocity, for defining the atmospheric extinction coefficient.

30. The observing system of claim 29 in which said coefficient defining means includes means, responsive to said detecting means, for subtracting signals due to scattered radiation detected when at least one precipitating particle is resolved from scattered radiation detected during the remainder of the sampling period when such a particle is not resolved.

31. The observing system of claim 30 in which said coefficient defining means includes means for averaging said scattered radiation signals and means for averaging the output of the subtracting means.

32. The observing system of claim 31 in which said coefficient defining means includes means for obtaining the total extinction coefficient from the average of the scattered radiation signals and means for obtaining the extinction coefficient due to suspended particles from the average of the output of the subtracting means.

33. The observing system of claim 32 further including a humidity sensor for sensing relative humidity and means, responsive to said humidity sensor and said means for obtaining, for identifying the type of suspended particles within the sample volume by matching the extinction coefficient due to suspended particles with predetermined values for types of suspended particles and with the relative humidity.

34. The observing system of claim 30 in which said means for defining the extinction coefficient includes means responsive to said detecting means for providing said scattered radiation signals in DC analog form.

35. A method of identifying the type of precipitation comprising:
providing a beam of radiation in the atmosphere;
detecting scattered radiation in a sample volume of the beam;
resolving at least one precipitating particle from suspended particles;
generating a peak signal value and a time-in-sample value for a resolved particle;
determining particle size from the peak signal value;
determining velocity from the time-in-sample value; and
matching size and velocity of the particle with predetermined values of precipitation particle sizes and velocities.

36. The method of claim 35 further including:
discerning the volume of said precipitating particle; and
summing the volumes of more than one precipitating particle over a known time period to determine the amount of precipitation.

37. The method of claim 35 further including:
subtracting signals due to scattered radiation detected when at least one precipitating particle is resolved from scattered radiation detected during the remainder of a sampling period when such a particle is not resolved to provide signals due to suspended particles;
averaging the scattered radiation signals;
averaging the suspended-particle signals;
obtaining the total extinction coefficient from the average of the scattered radiation signals; and
obtaining the extinction coefficient due to suspended particles from the average of the suspended-particle signals.

38. The method of claim 37 further including sensing the relative humidity and identifying the type of suspended particle within the sample volume by matching the extinction coefficient due to suspended particles with predetermined values for types of suspended particles and with the relative humidity.

* * * * *